United States Patent
Inoue et al.

(10) Patent No.: US 6,303,012 B1
(45) Date of Patent: *Oct. 16, 2001

(54) GAS SENSOR, GAS SENSOR SYSTEM USING THE SAME

(75) Inventors: Ryuji Inoue, Gifu; Shoji Kitanoya, Aichi; Kenji Kato, Aichi; Tomohiro Fuma, Aichi; Takafumi Oshima, Aichi, all of (JP)

(73) Assignee: NGK Spark Plug Co., Ltd., Nogoya (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/158,147

(22) Filed: Sep. 22, 1998

(30) Foreign Application Priority Data

Sep. 22, 1997 (JP) .................................. 9-275065
Jul. 29, 1998 (JP) ................................. 10-213651

(51) Int. Cl.⁷ ............................................ G01N 27/407
(52) U.S. Cl. .......................... 204/425; 204/426; 204/427
(58) Field of Search .................................. 204/421–429

(56) References Cited

U.S. PATENT DOCUMENTS

| | | | |
|---|---|---|---|
| 4,722,779 | * | 2/1988 | Yamada et al. ............... 204/426 |
| 5,304,294 | * | 4/1994 | Wang et al. ................... 204/426 |
| 5,866,799 | * | 2/1999 | Kato et al. .................... 204/425 |
| 5,935,398 | * | 8/1999 | Taniguchi et al. ............. 204/426 |

FOREIGN PATENT DOCUMENTS

| | | |
|---|---|---|
| 0 517 364 | 12/1992 | (EP) . |
| 0 731 351 A2 | 9/1996 | (EP) . |
| 0 797 094 A2 | 9/1997 | (EP) . |
| 0 851 225 A2 | 7/1998 | (EP) . |
| 4-290955 | 10/1992 | (JP) . |

OTHER PUBLICATIONS

European Search Report for EP 98117911 dated Nov. 20, 2000.

* cited by examiner

Primary Examiner—T. Tung
(74) Attorney, Agent, or Firm—Sughrue, Mion, Zinn, Macpeak & Seas, PLLC

(57) ABSTRACT

The gas sensor 1 has the following constituent features: (1) first processing space 9: a measurement gas is introduced thereinto via a first gas passage 11; (2) second processing space 10: a gas contained in the first processing space 9 is introduced thereinto via a second gas passage 13; (3) oxygen concentration detection element 4: adapted to measure the oxygen concentration of a gas contained in the first processing space 9; (4) oxygen pumping element 3: adapted to reduce the oxygen concentration of the measurement gas introduced into the first processing space 9 within a range such that water vapor contained in the measurement gas is not substantially decomposed; (5) oxidation catalyst section 16: adapted to accelerate combustion of a combustible gas component contained in a gas introduced into the second processing space 10; and (6) combustible gas component concentration detection element 5: a constant voltage is applied thereto, and element 5 has an output current which varies according to the amount of oxygen consumed by combustion of a combustible gas component contained in the gas introduced into the second processing space 10 from the first processing space, to thereby provide information regarding the concentration of the combustible gas component of the measurement gas based on the output current.

18 Claims, 28 Drawing Sheets

| ID\IP | IP1 | IP2 | IP3 | IP4 | ... |
|---|---|---|---|---|---|
| ID1 | C11 | C12 | C13 | C14 | ... |
| ID2 | C21 | C22 | C23 | C24 | ... |
| ID3 | C31 | C32 | C33 | C34 | ... |
| ID4 | C41 | C42 | C43 | C44 | ... |
| ⋮ | ⋮ | ⋮ | ⋮ | ⋮ | |

GAS SENSOR, GAS SENSOR SYSTEM USING THE SAME

FIELD OF THE INVENTION

The present invention relates to a gas sensor, a gas sensor system using the same, and a method of manufacturing the gas sensor.

BACKGROUND OF THE INVENTION

Resistance-type sensors are known for measuring the concentration of a combustible gas component such as hydrocarbon (HC) or CO contained in the exhaust gas of an automobile or the like. For example, an oxide semiconductor (n type) such as $SnO_2$ or the like is used as a sensing element for measuring the concentration of a combustible gas component such as HC or CO. Specifically, oxygen in the atmosphere adsorbs onto the sensing element through an effect induced by negative charges. When the atmosphere contains a combustible gas component such as HC or CO, the combustible gas component undergoes a combustion reaction with the adsorbed oxygen, thereby causing oxygen to be desorbed from the sensing element. Because a change in electric resistance of the sensing element associated with the oxygen desorption depends on the combustible gas component concentration of the atmosphere, the combustible gas component concentration of the atmosphere can be obtained by measuring the change in electric resistance. However, such a resistance-type sensor has a drawback in that an output from the sensing element formed of an oxide semiconductor is likely to vary depending on the concentration of oxygen or water vapor contained in the exhaust gas. Accordingly, even when the combustible gas component concentration remains unchanged, the sensor output value indicative of the combustible gas component concentration varies depending on, for example, the oxygen concentration of the exhaust gas.

In order to solve the above problem, an apparatus for measuring a combustible gas component concentration having the following structure is disclosed in Japanese Patent Application Laid-Open No. 8-247995. In this apparatus, the sensing element has two processing zones. An exhaust gas is introduced into a first processing zone via a first diffusion-controlling means. Oxygen is pumped out from the first processing zone by means of a first oxygen pumping element so as to reduce the oxygen concentration of the first processing zone to a low value at which combustible gas components are not substantially burned. Next, the gas having the thus-reduced oxygen concentration is introduced into a second processing zone via a second diffusion-controlling means. Oxygen is pumped into the second processing zone by means of a second oxygen pumping element so as to burn the combustible gas component. The combustible gas component concentration is determined based on the value of current flowing through or voltage developed across the second oxygen pumping element.

However, in the apparatus disclosed in the above-described patent publication, the second oxygen pumping element is operated such that the oxygen concentration of the second processing zone falls within a certain constant range. Accordingly, in addition to the second oxygen pumping element, the use of an element (for example, an oxygen concentration cell element) for measuring the oxygen concentration of the second processing zone is substantially unavoidable. Accordingly, the number of required elements for the second processing zone increases, thereby resulting in a complicated sensor structure and an increase in manufacturing cost.

Also, in the above disclosed apparatus, the oxygen concentration of the exhaust gas introduced into the first processing zone is reduced by means of the first oxygen pumping element to "a low value at which a combustible gas component is not substantially burned". According to this publication, the low value is not higher than $10^{-14}$ atm, preferably not higher than $10^{-16}$ atm, and is normally about $10^{-20}$ atm. However, when the oxygen concentration of the first processing zone is set at such a low value, the following problem arises related to accuracy in measuring the combustible gas component concentration.

Specifically, an exhaust gas generally contains a fair amount of water vapor in addition to combustible gas components such as hydrocarbon, carbon monoxide and hydrogen. Generally, the amount of water vapor varies according to operating conditions of an internal combustion engine. According to studies conducted by the present inventors, when the oxygen concentration of such an exhaust gas is reduced to the above-mentioned value, a portion of the water vapor is decomposed into hydrogen and oxygen. The thus-generated oxygen is pumped out from the first processing zone by means of the first oxygen pumping element, whereas the thus-generated hydrogen is not pumped out, but introduced into the second processing zone where the hydrogen induces combustion. When the gas to be measured (also referred to as an object gas) contains a combustible gas component composed primarily of hydrocarbon, the combustion of hydrogen generated by the decomposition of water vapor significantly affects accuracy in measuring the hydrocarbon concentration. Notably, the measurement examples disclosed in the above patent publication were all conducted under conditions where the water vapor concentration of the object gas was constant, and did not take into account the influence of a variation in water vapor concentration when measuring a combustible gas component concentration.

As disclosed in the above patent publication, a proton pump may be additionally used in order to pump out the thus-generated hydrogen from the first processing zone, so that only HC is selectively burned to thereby improve measurement accuracy. However, this method merely employs the proton pump as a means of last resort for coping with hydrogen generation associated with decomposition of water vapor. Addition of the proton pump makes the sensor structure and sensor control mechanism complex, causing an increase in apparatus cost. Furthermore, residual hydrogen which the proton pump has failed to pump out may induce a measurement error.

Also, the following problem is encountered. With the recent tendency of tightening exhaust gas regulations for air pollution control, internal combustion engines such as gasoline engines, diesel engines and the like engines tend to shift to lean-burn operation in order to suppress generation of HC associated with incomplete combustion. An exhaust gas produced under lean-burn conditions has an oxygen concentration higher than that produced under stoichiometric or rich conditions. When the above-described conventional apparatus is applied to such an exhaust gas, an oxygen pumping element is significantly burdened in order to reduce the oxygen concentration to the above-mentioned low value. As a result, the service life of the oxygen pumping element is shortened. Furthermore, since the operating power of the oxygen pumping element must be increased, a high output peripheral control circuit must also be used which in turn increases the apparatus cost.

SUMMARY OF THE INVENTION

It is therefore a first object of the present invention to provide a gas sensor and a method of manufacturing a gas sensor, having a simple structure and capable of accurately measuring the combustible gas component concentration of a measurement gas, such as an exhaust gas, despite variations in the oxygen concentration of the measurement gas and despite variations in element temperature, as well as to provide a gas sensor system using the gas sensor. A second object of the present invention is to provide a gas sensor and a method of manufacturing the gas sensor in which accuracy in measuring a combustible gas component concentration is less susceptible to decomposition of water vapor and which is suitably applicable to lean-burn conditions, as well as to provide a gas sensor system using the gas sensor.

The above objects of the present invention have been achieved by providing a gas sensor having the following characteristic features.

(1) First processing space: A first processing space is provided which is isolated from the surrounding environment. A measurement gas is introduced into the first processing space via a first gas passage.

(2) Second processing space: A second processing space is provided which is isolated from the surrounding environment. A gas contained in the first processing space is introduced into the second processing space via a second gas passage.

(3) Oxygen concentration detection element: Adapted to measure the oxygen concentration of a gas contained in the first processing space.

(4) Oxygen pumping element: Formed of an oxygen-ion conductive solid electrolyte. Electrodes are formed on opposing surfaces of the oxygen pumping element. The oxygen pumping element pumps out oxygen from the first processing space or pumps oxygen into the first processing space so as to reduce the oxygen concentration of the measurement gas introduced into the first processing space and measured by the first oxygen concentration detection element to a predetermined level.

(5) Oxidation catalyst element: Adapted to accelerate combustion of a combustible gas component contained in the gas which has been introduced into the second processing space from the first processing space via the second gas passage.

(6) Combustible gas component concentration detection element: Formed of an oxygen-ion conductive solid electrolyte. Electrodes are formed on opposing surfaces of the combustible gas component concentration detection element. One of the electrodes is arranged so as to be exposed to the second processing space. A constant voltage is applied to the combustible gas component concentration detection element via the electrodes. The combustible gas component concentration detection element has an output current which varies according to the amount of oxygen consumed by combustion of the combustible gas component, to thereby provide information regarding the concentration of the combustible gas component of the measurement gas.

The above objects of the present invention have also been achieved by providing a gas sensor system having the following constituent features.

(A) Gas sensor: Configured to have the following characteristic features.

(1) First processing space: A first processing space is provided which is isolated from the surrounding environment. A measurement gas is introduced into the first processing space via a first gas passage.

(2) Second processing space: A second processing space is provided which is isolated from the surrounding environment. A gas contained in the first processing space is introduced into the second processing space via a second gas passage.

(3) Oxygen concentration detection element: Adapted to measure the oxygen concentration of a gas contained in the first processing space.

(4) Oxygen pumping element: Formed of an oxygen-ion conductive solid electrolyte. Electrodes are formed on opposing surfaces of the oxygen pumping element. The oxygen pumping element pumps out oxygen from the first processing space or pumps oxygen into the first processing space.

(5) Oxidation catalyst element: Adapted to accelerate combustion of a combustible gas component contained in a gas having an oxygen concentration which has been adjusted by the oxygen pumping element and then introduced into the second processing space from the first processing space via a second gas passage.

(6) Combustible gas component concentration detection element: Formed of an oxygen-ion conductive solid electrolyte. Electrodes are formed on opposing surfaces of the combustible gas component concentration detection element. One of the electrodes is arranged so as to be exposed to the second processing space. A constant voltage is applied to the combustible gas component concentration detection element via the electrodes. The combustible gas component concentration detection element has an output current which varies according to the amount of oxygen consumed by combustion of the combustible gas component, to thereby provide information regarding the concentration of the combustible gas component of the measurement gas.

(B) Oxygen pumping operation control means: Adapted to control the oxygen pumping element so as to reduce the oxygen concentration of the measurement gas introduced into the first processing space and measured by the oxygen concentration detection element to a predetermined value.

(C) Voltage source: Adapted to apply a constant voltage to the combustible gas component concentration detection element.

The gas sensor and the gas sensor system of the present invention can measure a combustible gas component selected singly or in combination from the group consisting of, for example, hydrocarbon (HC), carbon monoxide and hydrogen.

In the configuration described above, the oxygen concentration of a measurement gas contained in the first processing space is adjusted to a predetermined value by operation of the oxygen pumping element. The thus-treated gas is introduced into the second processing space, where a combustible gas component undergoes combustion through the aid of the oxidation catalyst. The combustible gas component concentration detection element, to which a small constant voltage is applied, has an output current which varies according to the oxygen consumption due to combustion of the combustible gas component. Thus, based on the output current, information regarding the combustible gas component concentration of the original measurement gas is obtained. Because the oxygen concentration of a measurement gas detected by the oxygen concentration detection element is adjusted to a predetermined level before the combustible gas component concentration of the gas is measured, the output from the combustible gas component concentration detection element is less affected by the original oxygen concentration of the measurement gas. Thus, the relationship between the output current of the combustible gas component concentration detection element and the combustible gas component concentration of the measurement gas exhibits good linearity. Furthermore, in the conventional sensor disclosed in the above publication, at least two elements, namely the oxygen pumping element and the oxygen concentration measuring element, must be provided for the second processing zone (corresponding to the second processing space in the present invention). By contrast, in the configuration of the present invention, the combustible gas component concentration detection element suffices in and of itself, thereby simplifying sensor structure. Thus, the above-mentioned configuration achieves the first object of the present invention.

The above-described small constant voltage can be applied to the combustible gas component concentration detection element in a polarity which generates in the combustible gas component concentration detection element an oxygen pumping current which flows in a direction causing oxygen to be pumped out from the second processing space. In this case, the applied voltage is preferably adjusted such that a partial pressure of oxygen in the gas introduced into the second processing space does not cause a substantial decomposition of nitrogen oxides contained in the gas. This prevents a reduction in accuracy in measuring a combustible gas component concentration which would otherwise result from oxygen generated from the decomposition of NOx.

In the above-described gas sensor of the present invention, the oxygen pumping element can adjust the oxygen concentration of the measurement gas introduced into the first processing space and detected by the oxygen concentration detection element within a range such that water vapor contained in the measurement gas is not substantially decomposed. In this case, the oxygen pumping operation control means of the gas sensor system controls the operation of the oxygen pumping element such that the oxygen concentration of the measurement gas introduced into the first processing space and measured by the oxygen concentration detection element is adjusted within a range such that water vapor contained in the measurement gas is not substantially decomposed. Namely, within a range which does not substantially initiate a reaction of decomposing water vapor contained in the measurement gas.

By substantially suppressing hydrogen generation associated with the decomposition of water vapor by oxygen concentration adjustment, a loss in accuracy in measuring a combustible gas component concentration can be prevented which would otherwise result from combustion of the generated hydrogen. Also, the gas sensor and the gas sensor system of the present invention exhibit excellent selectivity toward HC, particularly methane, and thus can measure methane concentration more accurately than do conventional gas sensors. Thus, the second object of the present invention has been achieved.

When a measurement gas contains carbon dioxide and the carbon dioxide is decomposed, carbon monoxide which is a combustible gas component is generated as in the case of water vapor which generates hydrogen. Combustion of the thus-generated carbon monoxide may lower the accuracy in detecting the combustible gas component. In this case, the first oxygen pumping element preferably adjusts the oxygen concentration of the measurement gas introduced into the first processing space and detected by the oxygen concentration detection sensor within a range such that carbon dioxide is not substantially decomposed. Because the oxygen concentration at which decomposition of carbon dioxide occurs is generally lower than the oxygen concentration at which decomposition of water vapor occurs, the decomposition of carbon dioxide is concurrently prevented by employing an oxygen concentration which prevents decomposition of the water vapor.

The oxygen pumping element can be configured to adjust the oxygen concentration of the measurement gas introduced into the first processing space within a range of $10^{-12}$ atm to $10^{-6}$ atm. In this case, the oxygen pumping operation control means of the gas sensor system controls the operation of the oxygen pumping element such that the oxygen concentration of the measurement gas introduced into the first processing space and measured by the oxygen concentration detection element is adjusted within a range of $10^{-12}$ atm to $10^{-6}$ atm.

In the above-described configuration, the oxygen concentration of the first processing space achieved by operation of the oxygen pumping element is adjusted so as to fall within the above range, thereby suppressing the decomposition of water vapor and thus improving the sensing accuracy of the gas sensor or the gas sensor system. Because the oxygen concentration to be achieved by adjustment is far higher than the conventionally required oxygen concentration of $10^{-20}$ atm to $10^{-14}$ atm, the oxygen pumping element assumes a smaller burden even when measuring, for example, under lean-burn conditions. Thus, the service life of the oxygen pumping element is extended. Also, the power needed to operate the oxygen pumping element is not very high, and a control circuit and other peripheral devices can be provided at low cost. Also, in this case, the oxygen pumping element (or the oxygen pumping control means) is preferably configured such that the oxygen concentration of a measurement gas introduced into the first processing space and measured by the oxygen concentration detection element is adjusted to within a range such that water vapor contained in the measurement gas is not substantially decomposed. In the gas sensor and the gas sensor system described above, in order to further effectively prevent the decomposition of water vapor, the oxygen pumping element is preferably operated such that the oxygen concentration of the first processing space is adjusted to a value at which a portion of the combustible gas component is burned in the first processing space while the first electrode serves as an oxidation catalyst.

Furthermore, when the detection selectivity toward hydrocarbon (especially, methane or the like having a relatively low combustion activity) needs to be improved, the oxygen concentration within the first processing space as measured by the oxygen concentration detection element is preferably adjusted to fall within a range such that a component (e.g., carbon monoxide, hydrogen, ammonia) having a higher combustion activity than the hydrocarbon to be detected is burned more readily than hydrocarbon. This adjustment improves the detection selectivity toward hydrocarbon (e.g., methane). The oxygen concentration range varies depending on the combustion catalytic activity of the first and third electrodes, described below, toward various combustible gas components. However, the oxygen concentration range is generally $10^{-12}$–$10^{-6}$ atm, preferably $10^{-11}$–$10^{-9}$ atm.

When the oxygen concentration of a measurement gas introduced into the first processing space becomes less than $10^{-12}$ atm, the decomposition of water vapor, if present, becomes conspicuous. As a result, hydrogen generated by the decomposition of water vapor may significantly impair accuracy in measuring a combustible gas component concentration. By contrast, when the oxygen concentration of the first processing space is in excess of $10^{-6}$ atm, combustion of a combustible gas component becomes conspicuous in the first processing space. Accordingly, the combustible gas component concentration of a gas introduced into the second processing space becomes small with a potential failure to attain a predetermined measurement accuracy. More preferably, the oxygen concentration of the first processing space is adjusted to a value of $10^{-11}$ atm to $10^{-9}$ atm.

For example, when the gas sensor is set at a working temperature of 650° C. to 700° C. and the water vapor concentration of a measurement gas varies within a range of about 5% to 15%, oxygen that maintains equilibrium with water vapor and hydrogen has a minimum partial pressure of about $10^{-12}$ atm. When the partial pressure of oxygen drops below the minimum value, decomposition of water vapor progresses, thereby affecting accuracy in measuring a combustible gas component concentration. Therefore, in this case, the oxygen concentration of the first processing space is preferably set to a value greater than the above minimum partial pressure of oxygen.

As used herein, unless specifically described otherwise, the oxygen concentration within the first processing space means the oxygen concentration measured by the oxygen concentration detection element. For example, when a part of a combustible gas component contained in a measurement gas burns and consumes oxygen, the oxygen concentration measured by the oxygen concentration detection element is not necessarily equal to the oxygen concentration before oxygen is consumed due to combustion. Also, the oxygen concentration may vary at locations within the first processing space due to the presence of a porous electrode that is disposed to face the first processing space and catalyzes combustion of a combustible gas component, or due to oxygen pumping of the oxygen pumping element. In this case as well, the oxygen concentration detection element is considered to represent the oxygen concentration within the first processing space. When the oxygen concentration of a measurement gas introduced into the first processing space is relatively high, the first oxygen pump operates to mainly pump oxygen out from the first processing space in order to cause the oxygen concentration detected by the oxygen concentration detection element to fall within the range of $10^{-12}$–$10^{-6}$ atm. By contrast, the first oxygen pump operates to pump oxygen into the first processing space when an increased amount of a combustible gas component (e.g., carbon monoxide, hydrogen, ammonia) burns while the first electrode, described below, is used as a catalyst for combustion, and oxygen consumption due to combustion proceeds.

In the gas sensor (and the gas sensor system) described above, at least either the first gas passage for introducing a measurement gas into the first processing space or the second gas passage for establishing communication between the first processing space and the second processing space may be configured as a diffusion-controlling passage for permitting gas flow at a constant diffusion resistance. This feature suppresses the compositional variation of a gas introduced into the first or second processing space to a small degree for a constant period of time determined by the diffusion resistance of the passage even when the composition of the measurement gas varies. Thus, accuracy in measuring the concentration of a combustible gas component concentration can be improved. Specifically, the diffusion-controlling passage may assume the form of small holes or slits or may be formed of any of various throttling mechanisms or porous metals or ceramics having communicating pores formed therein.

In the gas sensor and the gas sensor system described above, the oxygen concentration detection element may be an oxygen concentration cell element. The oxygen concentration cell element is formed of an oxygen-ion conductive solid electrolyte having electrodes formed on both (opposing) surfaces thereof. One of the electrodes is disposed so as to be exposed to the first processing space. In this case, the electrode exposed to the first processing space is defined as a first electrode, and the electrode of the combustible gas component concentration detection element exposed to the second processing space is defined as a second electrode. The first and second electrodes may each assume the form of a porous electrode having oxygen molecule desorption capability. The second electrode can be adapted to serve as the above-described oxidation catalyst section having oxidation-related catalytic activity toward a combustible gas component contained in the measurement gas.

In the above configuration, the first electrode has an oxidation-related catalytic activity that is lower than that of the second electrode. Thus, at least a portion of a residual combustible gas component which has not been burned in the first processing space can be reliably burned in the second processing space, thereby improving sensor sensitivity. Furthermore, because the electrode (second electrode) of the combustible gas component concentration detection element exposed to the second processing space also serves as an oxidation catalyst section, the structure of the gas sensor or the gas sensor system is further simplified.

A porous metal layer other than the second electrode may be formed on a wall portion which, together with other portions, defines the second processing space, in such manner as to be exposed to the second processing space. The porous metal layer serves as the oxidation catalyst section exhibiting oxidation-related catalytic activity toward a combustible gas component contained in the measurement gas. This feature improves the efficiency of combustion of a combustible gas component in the second processing space and thus improves the sensitivity of the gas sensor. Furthermore, the porous metal layer may be used as a porous electrode for another application (for example, as a porous electrode of an oxygen pumping element or oxygen concentration cell element other than those of the present invention).

When the gas component to be measured is CO or HC, an electrode having higher oxidation-related catalytic activity may be formed of Pt, Pd, Rh, a Pt alloy, a Pd alloy, an Rh alloy, a Pt—Rh alloy, an Rh—Pd alloy, a Pd—Ag alloy, or a like metal (hereinafter these metals are referred to as metals of a high-activity metal group). An electrode having lower oxidation-related catalytic activity may be formed of Au, Ni, Ag, an Au alloy, an Ni alloy, an Ag alloy, a Pt—Pd alloy, a Pt—Au alloy, a Pt—Ni alloy, a Pt—Ag alloy, an Ag—Pd alloy, an Au—Pd alloy, or a like metal (hereinafter these metals are referred to as metals of a low-activity metal group). When a $ZrO_2$ solid electrolyte, described below, is used as an oxygen-ion conductive solid electrolyte constituting a main portion of the oxygen pumping element, the oxygen concentration cell element, or the combustible gas component concentration detection element, a metal of the low-activity metal group is preferably selected such that it can be fired with the $ZrO_2$ solid electrolyte (firing temperature: 1450° C. to 1500° C.), in view of improving in sensor-manufacturing efficiency. For example, when a Pt—Au alloy is used, the Au contents thereof may be 0.1% to 3% by weight. When the Au content is less than 0.1% by weight, an electrode formed of the alloy may have an excessively high oxidation-related catalytic activity. By contrast, when Au is added in excess of 3% by weight, the amount of Au volatilizing from the alloy during firing increases, thus increasing the amount of wasted Au.

In the gas sensor of the present invention, a more preferable result is obtained by employing an electrode having the following structure. Specifically, the oxygen pumping element is formed of an oxygen-ion conductive solid electrolyte having electrodes formed on both surfaces thereof, and one of the electrodes (hereinafter referred to as the "third electrode") is disposed so as to be exposed to the first processing space. When the component to be detected is CO or HC, the third electrode is composed of two layers, namely, a porous main electrode layer and a porous surface electrode layer. The porous main electrode layer is made of Pt—Au alloy (Au content: 1 wt. % or less) or Pt. The porous surface electrode layer covers the main electrode layer to thereby form a surface layer portion of the third electrode. The surface electrode layer is made of a material selected from the group consisting of a metal containing Au or Ag as a main component, a Pt—Au alloy, an Au—Pd alloy, a Pt—Ag alloy and a Pt—Ni alloy (hereinafter collectively referred to as "inactive metal"). The third electrode has a lower oxidation-related catalytic activity toward the combustible gas component than does the second electrode. As used herein, the term "X-Y alloy" means an alloy in which a metal component having the highest content by weight is X, and a metal component having the second highest content by weight is Y. The alloy may be an X-Y binary system alloy or a higher-order system alloy containing X, Y and other alloy components.

Materials for the electrodes of the oxygen concentration cell element or the oxygen pumping element must have a sufficient catalytic activity for desorption and recombination of oxygen molecules. Pt single metal, for example, is an excellent material in this point. However, if this material is used for the electrode exposed to the first processing space, the material has an extremely high combustion catalytic activity toward a combustion gas component. Therefore, the catalytic activity must be decreased slightly. For example, as conventionally practiced, Au, whose combustion catalytic activity is low, is mixed with Pt in an amount of up to about 20 wt. %, thereby forming a Pt—Au alloy. However, when the Au content increases, a considerable decrease in activity for desorbing oxygen molecules occurs concurrently with a decrease in the combustion catalytic activity toward a combustible gas component. Therefore, these two catalytic activities are difficult to balance.

This problem can be solved by employing the above-described multilayer electrode, in which the surface of the porous main electrode layer formed of a Pt—Au alloy or Pt having a high activity for desorbing oxygen molecules is covered with the porous surface electrode layer formed of an inactive metal having a low combustion catalytic activity toward a combustible gas component. This structure allows for a convenient adjustment to decrease the combustion catalytic activity toward a combustible gas component to the extent possible, while maintaining a sufficient level of oxygen molecule desorption activity.

In the present invention, the surface electrode layer is preferably formed of an Au-containing porous metal that has a considerably low combustion catalytic activity toward CO or HC and some degree of catalytic activity for desorption and recombination of oxygen molecules. Alternatively, a porous metal containing Ag as a main component, a porous Pt—Au alloy (Au content: 5 wt. % or more), a porous Pt—Pb alloy (Pb content: 1 wt. % or more), a porous Pt—Ag alloy (Ag content: 1 wt. % or more), a porous Pt—Ni alloy (Ni content: 1 wt. % or more), and the like may be used.

The surface electrode layer and the main electrode layer may be arranged such that these layers are into indirect contact with each other via one or more other layers. However, the use of a two-layer structure comprising the main electrode layer and the surface electrode layer simplifies the manufacturing process. In this case, when the surface electrode layer is formed of an Au-containing porous metal that contains Au as a main component, the remarkable effect of suppressing the combustion catalytic activity toward a combustible gas component can be obtained, while a sufficient level of oxygen molecule desorption activity is also maintained.

The above-described multilayer electrode is advantageously employed as the third electrode of the oxygen pump which does not require a sharp response to oxygen concentration. The above-described multilayer electrode can be used as the first electrode of the oxygen concentration cell element. However, in order to further improve accuracy in detecting the oxygen concentration within the first processing space using the oxygen concentration cell element, the first electrode is preferably formed of Pt, a Pt—Au alloy or a Pt—Ag alloy. In this case, because combustion of a combustible gas component that is caused by the first electrode within the first processing space can be suppressed by making the area of the first electrode smaller than that of the third electrode, the loss caused by combustion of the combustible gas component within the first processing space can be decreased, so that the sensor sensitivity can be further increased.

When a Pt—Au alloy or a Pt—Ag alloy is used as the first electrode, Au or Ag is added in order to suppress the combustion catalytic activity toward CO or HC. In this case, when the Au or Ag content exceeds 1 wt. %, the oxygen molecule desorption activity decreases excessively, resulting in a deteriorated oxygen concentration detection performance. By contrast, when the Au or Ag content is less than 1 wt. %, almost no effect of suppressing the combustion catalytic activity is expected. Au and Ag may be added together to Pt such that their total content does not exceed 1 wt. %.

When detection selectivity for hydrocarbon among various combustible gas components must be improved, components having a higher combustion activity than hydrocarbon are preferably burned more readily than the hydrocarbon to be detected. In this case, as described above, the oxygen concentration within the first processing space as measured by the oxygen concentration detection element is adjusted. Furthermore, the combustion catalytic activity of first electrode or the third electrode exposed to the first processing space and the temperature within the first processing space are important factors in improving the measurement selectivity. When the third electrode is formed of the above-described multilayer electrode having a relatively low combustion catalytic activity and the first electrode is formed of Pt or a Pt alloy having a high combustion catalytic activity, a hydrocarbon component (e.g., methane) having a slightly low combustion activity does not burn much, while components such as carbon monoxide, hydrogen and ammonia which have a higher combustion activity readily burn on the first electrode. As a result, an environment convenient for selective measurement of hydrocarbon components is created. When the temperature within the first processing space increases, the combustion reaction proceeds easily, and the difference in combustion catalytic activity between electrodes made of different materials is not so apparent. This is disadvantageous for the selective measurement of hydrocarbon components. However, when the third electrode has the above-described multilayer structure, a considerably large difference in catalytic activity between the third electrode and the first electrode formed of Pt or the like is produced even at considerably high temperatures (e.g. 700–800° C.), so that selective detection of hydrocarbon components can be performed effectively.

When the third electrode is formed into the above-describe multilayer structure, the gas sensor of the present invention can be manufactured in accordance with a method comprising the following steps.

(1) a substrate electrode layer forming step which comprises forming a substrate electrode pattern containing an unfired layer of material powder for the main electrode layer of the third electrode (hereinafter referred to as the "unfired main electrode layer") on an unfired compact of the oxygen-ion conductive solid electrolyte layer constituting said first oxygen pumping element (hereinafter referred to as the "unfired solid electrolyte compact"), and integrally firing the unfired main electrode layer with the unfired solid electrolyte compact at a first temperature to form on the oxygen-ion conductive solid electrolyte layer a substrate electrode layer containing the main electrode layer; and (2) a surface electrode layer forming step which comprises forming a layer of material powder for the surface electrode layer on the substrate electrode layer, and subjecting to secondary firing at a second temperature lower than the first temperature to thereby form the surface electrode layer. The layer of material power may be formed, for example, by applying a paste of the material powder onto the main electrode layer.

Because the substrate electrode layer containing the main electrode layer is formed of a high-melting point metal such as Pt or a Pt—Au or Pt—Ag alloy having the above-described composition, the substrate electrode layer can be fired concurrently with a solid electrolyte ceramic, such as zirconia, that constitutes the main portion of each element. However, when the surface electrode layer is formed of an Au-containing metal, which has a low melting point, maintaining the porous state of the substrate electrode layer becomes difficult when it is fired together with a solid electrolyte ceramic. In addition, Au diffuses into the substrate electrode layer, and therefore it becomes difficult to achieve the effect of suppressing the combustion catalytic activity. In order to solve this problem, the above-described process can be employed in which the surface electrode layer is subjected to secondary firing at a temperature lower than that used for integrally firing the substrate electrode layer and the solid electrolyte layer. This is to bond the surface electrode layer to the substrate electrode layer by baking. Thus, a multilayer electrode having the desired performance is obtained.

The components (e.g., Au) of the surface electrode layer may diffuse into the main electrode layer during the secondary firing or when the sensor is used at high temperature. For example, even if the main electrode layer is substantially formed of Pt, Au may diffuse from the surface electrode layer into the main electrode layer so that Au constituting the main electrode layer is converted into a Pt—Au alloy. If diffusion of the material of the surface electrode layer into the main electrode layer proceeds excessively, the thickness of the surface electrode layer becomes insufficient, or in an extreme case, the surface electrode layer disappears. For example, when the surface electrode layer is desirably formed mainly of Au and the main electrode layer is desirably formed mainly of Pt, the temperature for secondary firing is preferably set to about 800–1050° C. in order to prevent excessive diffusion of Au into the main electrode layer. When the secondary firing temperature is less than 800° C., firing of the surface electrode layer becomes insufficient with the possibility of delamination of the surface electrode layer due to inadequate contact. By contrast, when the secondary firing temperature is greater than 1050° C., the thickness of the surface electrode layer becomes insufficient due to diffusion of the Au component, or firing proceeds excessively such that the porous structure is lost. In this case, the oxygen permeability that the porous electrode must have becomes difficult to maintain. When Au is mixed in the constituent metal of the main electrode layer in an amount of about 3–10 wt. % (for example, 10 wt. %) from the beginning, the diffusion of Au from the surface electrode layer into the main electrode layer can be suppressed because the extent of solid solution formation of Au into Pt is relatively small (about 5 wt. %) at 800° C. Thus, the drawbacks such as a reduction in thickness of the surface electrode layer can be effectively avoided.

In a preferred embodiment, the manufacturing method comprising the above-described secondary firing step can be performed efficiently when the gas sensor of the present invention is constructed such that a pumping cell unit including the oxygen pumping element is formed separately from a sensor cell unit including the oxygen concentration detection element, the second processing space and the combustible gas component concentration detection element; and the pumping cell unit and the sensor cell unit are joined and integrated with each other via a bonding material. In this case, the pumping cell unit is manufactured by firing such that the substrate electrode layer is formed without forming the surface electrode layer; the secondary firing is performed in order to form the surface electrode layer on the substrate electrode layer of the pumping cell unit; and the pumping cell unit is integrated with the sensor cell unit which has been separately manufactured through firing. Thus, the gas sensor is obtained. Preferably, a pump-cell-side fitting portion is formed in the pumping cell unit, and a sensor-cell-side fitting portion for engaging with the pump-cell-side fitting portion is formed in the sensor cell unit. In this case, positioning during joining can be easily performed by engaging the pump-cell-side fitting portion and the sensor-cell-side fitting portion. Thus, the manufacturing efficiency of the sensor can be improved.

For stabilizing the sensor output, the electrode (second electrode) of the combustible gas component concentration detection element exposed to the second processing space be is preferably positioned so as not to interfere with or contact the second gas passage. When the electrode is in contact with the second gas passage, combustion of a combustible gas component may be initiated before equilibrium is established between a measurement gas which is newly introduced into the second processing space from the first processing space and a gas which is already present in the second processing space. When such positional interference is avoided, the above phenomenon is less likely to occur, thereby stabilizing the sensor output.

The oxygen concentration cell element or the combustible gas component concentration detection element may be formed of an oxygen-ion conductive solid electrolyte composed mainly of $ZrO_2$ ($ZrO_2$ solid electrolyte). In the oxygen concentration cell element formed of a $ZrO_2$ solid electrolyte, one electrode is in contact with a gas to be measured, which gas contains oxygen and a combustible gas component, while the other electrode is in contact with a reference atmosphere having a constant oxygen concentration. The electromotive force of the oxygen concentration cell element varies abruptly when the gas composition falls outside a stoichiometric composition in which oxygen and a combustible gas component are present in a proper ratio so that they completely react with each other. When an ordinary gasoline engine or diesel engine is operated under lean-burn conditions, a measurement gas emitted from the engine contains combustible gas components in a total concentration of about 0 to 1000 ppmC (ppmC: parts per million represented with carbon equivalent). A measurement gas having such a combustible gas component concentration is introduced into the first processing space, and the oxygen concentration of the thus introduced measurement gas is adjusted to $10^{-6}$ atm (preferably $10^{-9}$ atm) or lower, as described above. As a result, a gas introduced into the second processing space from the first processing space has a stoichiometric composition or a composition shifted slightly toward a rich condition. Thus, the output from the combustible gas component concentration detection element is increased, thereby improving the sensitivity of the gas sensor.

When the oxygen pumping element, the oxygen concentration cell element and the combustible gas component concentration detection element are formed of a $ZrO_2$ solid electrolyte as described above, a heating element may be provided for heating the elements to a predetermined working temperature. The working temperature may be set to 650° C. to 700° C. When the working temperature is in excess of 700° C., the output current value of the combustible gas component concentration detection element becomes excessively low, causing a reduction in sensitivity of the gas sensor. This is considered to occur because most of the combustible gas component, such as an HC component contained in a measurement gas, is burned in the first processing space due to the high working temperature. By contrast, when the working temperature is lower than 650° C., the internal resistance of the oxygen pumping element increases, causing unstable operation. As a result, accuracy in measuring a combustible gas component may be reduced.

As described above, in the gas sensor and the gas sensor system of the present invention, the oxygen concentration detection element may be an oxygen concentration cell element formed of an oxygen-ion conductive solid electrolyte having electrodes formed on both surfaces thereof, wherein one electrode (the first electrode) serves as a detection electrode and is exposed to the first processing space, while the other electrode serves as an oxygen reference electrode. In this case, the oxygen reference electrode may be used as an electrode of the combustible gas component concentration detection element having another electrode (second electrode) that is exposed to the second processing space. This arrangement enables the oxygen concentration cell element and the combustible gas component concentration detection element to share the oxygen reference electrode, to thereby implement a compact sensor.

More specifically, the first processing space and the second processing space may be arranged such that a partition wall formed of an oxygen-ion conductive solid electrolyte is disposed therebetween. In this case, the second gas passage is formed in the partition wall so as to establish communication between the first processing space and the second processing space. An oxygen reference electrode is embedded in the partition wall at a thicknesswise intermediate portion. The first electrode is formed on the partition wall so as to be exposed to the first processing space. The oxygen concentration cell element is formed by the first electrode, the oxygen reference electrode and a portion of the partition wall interposed between the first electrode and the oxygen reference electrode. Also, the second electrode is formed on the partition wall so as to be exposed to the second processing space. The combustible gas component concentration detection element is formed by the second electrode, the oxygen reference electrode and a portion of the partition wall interposed between the second electrode and the oxygen reference electrode. The oxygen pumping element is arranged opposite the partition wall with the first processing space disposed therebetween. This arrangement enables the oxygen concentration detection element and the combustible gas component concentration detection element to share the oxygen reference electrode, to thereby implement a compact sensor.

The oxygen reference electrode of the oxygen concentration cell element may be a self-generation type oxygen reference electrode in which a very small pumping current is applied between the detection electrode and the oxygen reference electrode in a direction such that oxygen is pumped toward the oxygen reference electrode side. As a result, a reference oxygen concentration of a predetermined level is established within the oxygen reference electrode by the pumped-in oxygen. This structure stabilizes the oxygen concentration at the oxygen reference electrode side, and allows for a more accurate measurement of the oxygen concentration.

Also, when the oxygen concentration cell element and the combustible gas component concentration detection element share the oxygen reference electrode and the oxygen reference electrode is designed to function as a self-generation type oxygen reference electrode, a current limit circuit is preferably provided to limit within a predetermined range the current flowing between the second electrode and the oxygen reference electrode. More specifically, the current limit circuit is designed to limit within a predetermined range the current flowing from the second electrode to the oxygen reference electrode.

Namely, the fact that a current flows from the second electrode to the oxygen reference electrode means that oxygen flows out from the oxygen reference electrode toward the second electrode. This is because the oxygen-ion conductive solid electrolyte is interposed between these electrodes. If the current flow is excessive, a large amount of oxygen flows out from the oxygen reference electrode, such that the oxygen reference electrode cannot maintain the required oxygen concentration. As a result, proper operation of the oxygen concentration cell element or proper control of the oxygen concentration within the first processing space becomes difficult, resulting in a decrease in the detection accuracy of the sensor. However, this drawback can be avoided by providing the above-described current limit circuit.

Furthermore, the current limit circuit may be designed to limit within a predetermined range the current flowing from the oxygen reference electrode to the second electrode. If the current flow is excessive, a large amount of oxygen flows into the oxygen reference electrode. As a result, the pressure within the oxygen reference electrode becomes excessively high such that the electrode may break. However, this problem can be avoided by providing the above-described current limit circuit.

In this case, at least either the oxygen reference electrode or the second electrode is preferably formed in or on the partition wall at a position so as not to contact the second gas passage. More preferably, both of the oxygen reference electrode and the second electrode are positioned so as not to contact the second gas passage. Positioning the second electrode in such a manner yields the aforementioned advantage. Also, positioning the oxygen reference electrode in such a manner prevents leakage of oxygen from the oxygen reference electrode through the second gas passage, thereby stabilizing the oxygen reference concentration and thus stabilizing the sensor output which is indicative of the combustible gas component concentration.

In the above gas sensor, the current flowing through the oxygen pumping element of the gas sensor, i.e., the oxygen pumping current, varies according to the oxygen concentration of the measurement gas. Accordingly, the oxygen pumping current is a measure of the oxygen concentration of the measurement gas. Therefore, in the gas sensor system of the present invention, correction means may be provided for correcting the output of the combustible gas component concentration detection element based on the oxygen concentration of the measurement gas as determined by the oxygen pumping current. That is, as described above, the gas sensor system of the present invention is characterized as being less susceptible to the oxygen concentration of a measurement gas. Nevertheless, when the oxygen concentration causes variations in the output, such variations can be corrected by the correction means, thereby further improving accuracy in measuring a combustible gas concentration.

Specifically, the correction means may include storage means and correction value determination means. The storage means stores information regarding the relationship between the output current of the combustible gas component concentration detection element and the combustible gas component concentration, relative to various values of oxygen concentration (or values of oxygen pumping current). The correction value determination means determines a corrected output current (or a corresponding combustible gas component concentration) based on the output current of the combustible gas component concentration detection element and the above information. Thus, the measured combustible gas component concentration can be corrected to take into account the oxygen concentration of the measurement gas.

BRIEF DESCRIPTION OF THE DRAWINGS

FIG. 9 is a view showing another example of a concentration conversion table.

FIG. 26(*b*) is a sectional view taken along line A—A; and

FIG. 26(*c*) is a sectional view taken along line B—B.

DESCRIPTION OF SYMBOLS

Figure 1A:
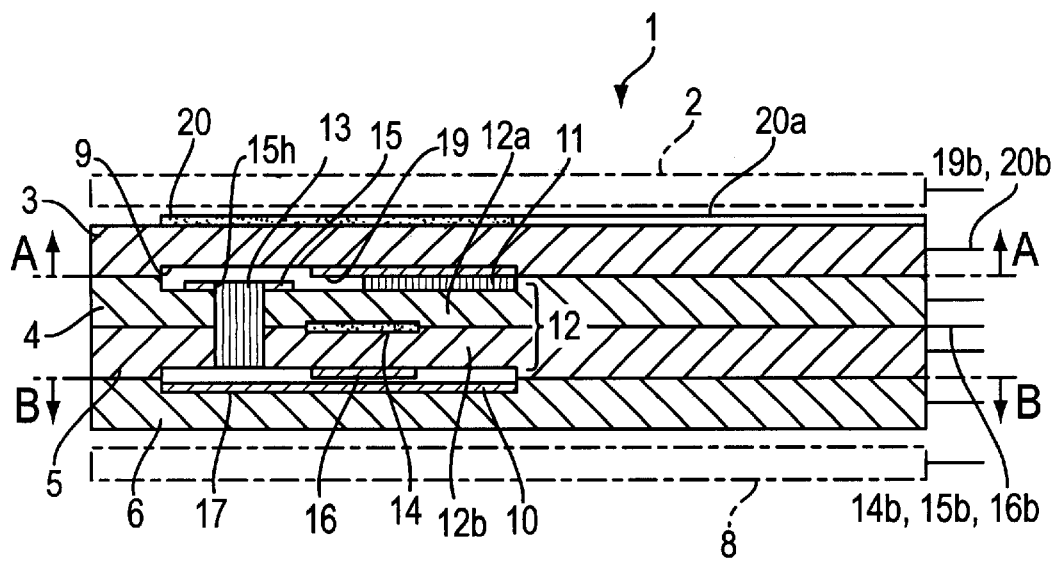
FIG. 1(*a*) is a sectional front view showing a gas sensor according to a first embodiment of the present invention, FIG. 1(*b*) is a sectional view taken along line A—A, and FIG. 1(*c*) is a sectional view taken along line B—B.

1: 100: gas sensor
2: first heater
3: oxygen pumping element
4: oxygen concentration cell element (oxygen concentration detection element)
5: combustible gas component concentration detection element
6: shield member
8: second heater
9: first processing space
10: second processing space
11: first gas passage
12: partition wall
13: second gas passage
14: oxygen reference electrode
15: first electrode
16: second electrode (oxidation catalyst section)
17: porous metal layer (oxidation catalyst section)
19: third electrode
50: gas sensor system
51: peripheral circuit
52: microprocessor
53: CPU (correction means)
54: ROM
55: RAM
56: I/O port
57: differential amplifier (oxygen pumping operation control means)
71: constant-voltage regulated DC power source (voltage application means)
120: current limit circuit
111: pumping cell unit
111*a*: fitting projections (pump-cell-side fitting portions)
112: sensor cell unit
112*a*: fitting depressions (sensor-cell-side fitting portions)
151: main electrode layer
152: surface electrode layer

DETAILED DESCRIPTION OF THE PREFERRED EMBODIMENTS

Various embodiments of the present invention will now be described with reference to the drawings and Examples, however, the present invention should not be construed as being limited thereto.

Figure 1B:
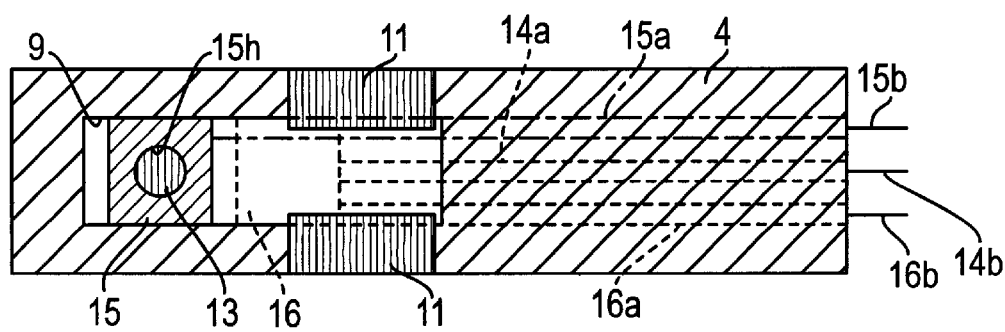
Figure 1C:
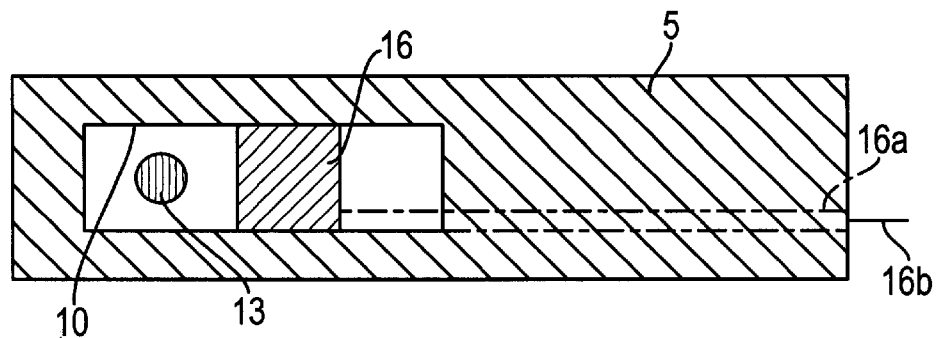

First Embodiment:

FIG. 1 shows a gas sensor 1 according to an embodiment of the present invention. The gas sensor 1 includes a first heater 2, an oxygen pumping element 3, an oxygen concentration cell element (oxygen concentration detection element) 4, a combustible gas component concentration detection element 5, a shield member 6, and a second heater 8. These elements of the gas sensor 1 are in the shape of an elongated sheet and arranged in layers in this order so as to be integrated into a single unit. A first processing space 9 is formed between the oxygen pumping element 3 and the oxygen concentration cell element 4. A second processing space 10 is formed between the combustible gas component concentration detection element 5 and the shield member 6. That is, the oxygen pumping element 3 and the oxygen concentration cell element 4 form a main portion of a first processing space, and the combustible gas component concentration detection element 5 and the shield member 6 form a main portion of a second processing space.

The elements 3 to 5 and the shield member 6 are formed of a solid electrolyte having oxygen-ion conductivity. A typical example of such a solid electrolyte is a $ZrO_2$ solid solution and $Y_2O_3$ or CaO. Another example is a solid solution of $ZrO_2$ and an oxide of an alkaline earth metal or of a rare earth metal. $ZrO_2$ serving as a base material may include $HfO_2$. The present embodiment employs a solid electrolyte ceramic of $ZrO_2$ obtained through solid solution of $Y_2O_3$ or CaO. The first and second heaters 2 and 8, respectively, are known ceramic heaters and are adapted to heat the elements 3 to 5 to a predetermined working temperature (650° C. to 700° C.). An insulating layer (not shown in FIG. 1; an insulating layer 260 is shown in FIG. 3) is interposed between the elements 3 to 5 and the shield member 6. The insulating layer is primarily formed of $Al_2O_3$. The laminated sensor structure is formed by laminating and subsequent firing of ceramic green sheets (ceramic moldings), which become the elements 3 to 6.

First gas passages 11 are formed at both side wall portions of the first processing space 9 so as to establish communication between the first processing space 9 and an external atmosphere to be measured. Located on both widthwise sides of the first processing space 9 as shown in FIG. 1(*b*), the first gas passages 11 are interposed between and extend along the oxygen pumping element 3 and the oxygen concentration cell element 4 in a longitudinal direction of the elements 3 and 4. The first gas passage 11 is formed of a porous ceramic body having communicating pores, which ceramic body is a porous fired body of $Al_2O_3$ or the like. Thus, the first gas passages 11 serve as diffusion-controlling passages for introducing a measurement gas into the first processing space 9 from the outside while a constant diffusion resistance is maintained.

The oxygen concentration cell element 4 and the combustible gas component concentration detection element 5 are arranged in adjacent layers. A partition wall 12, formed of an oxygen-ion conductive solid electrolyte, is interposed between the first processing space 9 and the second processing space 10. In other words, the first and second processing spaces 9 and 10, respectively, are arranged with the partition wall 12 interposed therebetween. A second gas passage 13 is formed in the partition wall 12 so as to establish communication between the first processing space 9 and the second processing space 10. An oxygen reference electrode 14 is embedded in the partition wall 12 at a thicknesswise intermediate portion. As in the case of the first gas passages 11, the second gas passage 13 is formed of a porous ceramic body and serves as a diffusion-controlling passage for introducing a gas into the second processing space 10 from the first processing space 9 while maintaining a constant diffusion resistance. The first and second gas passages 11 and 13, respectively, may assume the form of small holes or slits instead of being formed of a porous ceramic body (or a porous metallic body).

A first electrode 15 is formed on the partition wall 12 so as to be exposed to the first processing space 9. A main portion of the oxygen concentration cell element 4 includes the first electrode 15, the oxygen reference electrode 14 and a portion 12*a* of the partition wall 12 interposed between the electrodes 15 and 14. A second electrode 16 is formed on the partition wall 12 so as to be exposed to the second processing space 10. A main portion of the combustible gas component concentration detection element 5 includes the second electrode 16, the oxygen reference electrode 14 and a portion 12*b* of the partition wall 12 interposed between the electrodes 16 and 14. Also, the oxygen pumping element 3 has electrodes 19 and 20 formed on both surfaces thereof.

The electrodes 14 and 15 are positioned so as to be shifted from each other in a longitudinal direction of the oxygen concentration cell element 4.

The electrodes 14 to 16, 19 and 20 have a reversible catalytic function (oxygen desorption related catalytic function), which catalyzes a desorption reaction for desorbing oxygen molecules therefrom in order to introduce oxygen into solid electrolytes of the elements 3 to 5, and a recombination reaction for recombining with oxygen in order to make the solid electrolytes release oxygen. Materials for the electrode 19 of the oxygen pumping element 3 and the first electrode 15 of the oxygen concentration cell element 4, which electrodes 19 and 15 are exposed to the first processing space 9, and that for the second electrode 16 of the combustible gas component concentration detection element 5, which electrode 16 is exposed to the second processing space 10, are selected such that the electrodes 19 and 15 have lower catalytic activity with respect to oxidation (i.e., combustion) of a component to be measured, such as methane, than does the electrode 16. In the present embodiment, the electrodes 19 and 15 are formed of a Pt—Au alloy (for example, an alloy of Pt and 1% by weight of Au), and other electrodes are formed of Pt. These porous electrodes are formed in the following manner. In order to improve adhesion between an electrode and a substrate formed of a solid electrolyte ceramic, a metal or alloy powder serving as an electrode material is mixed with an appropriate amount of solid electrolyte ceramic powder similar to that used as the material for the substrate. The resulting mixture is formed into a paste. By using the paste, an electrode pattern is printed on a ceramic green sheet serving as a substrate, followed by firing. The electrodes 19 and 15 having lower oxidation-related catalytic activity may be formed of Au or a like metal which has an oxidation-related catalytic activity that is lower than that of a Pt—Au alloy. However, because a Pt—Au alloy and a solid electrolyte ceramic of $ZrO_2$ can be concurrently fired, the manufacturing efficiency of the gas sensor 1 is improved.

Figure 2:
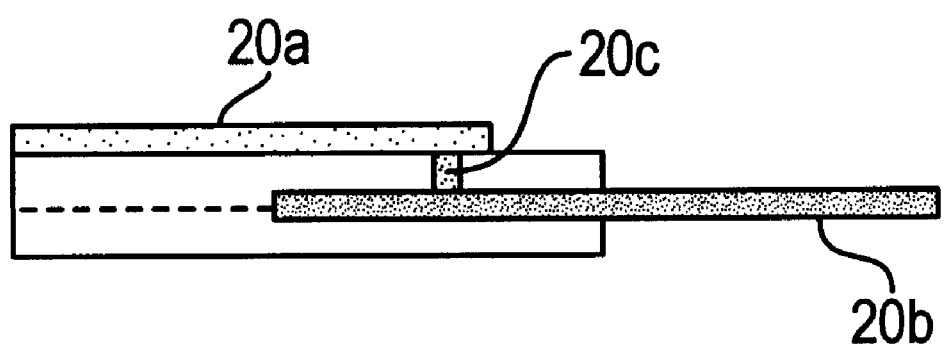
FIG. 2 is a sectional view showing an example connection between an electrode lead and a terminal.

As shown in FIG. 1, electrode leads 14a to 16a, 19a and 20a are integrally formed with the electrodes 14 to 16, 19 and 20, respectively, of the elements 3 to 5, and extend along a longitudinal direction of the elements 3 to 5 toward a sensor end portion. At the sensor end portion, ends of connection terminals 14b to 16b, 19b and 20b are embedded in the elements 3 to 5. As illustrated in FIG. 2, which representatively shows the electrode lead 20a, each connection terminal (20b) is electrically connected to an end portion of each electrode lead (20a) by means of a conductor (20c). The conductor (20c) is formed in the element thickness direction by sintering a metallic paste.

As shown in FIG. 1, the oxygen reference electrode 14 and the second electrode 16 of the combustible gas component concentration detection element 5 are positioned so as not to contact the second gas passage 13. This feature further stabilizes the sensor output indicative of combustible gas component concentration. The first electrode 15 of the oxygen concentration cell element 4 overlaps the second gas passage 13. In order to permit gas flow, a through-hole 15h is formed in the first electrode 15 at a position corresponding to the second gas passage 13.

Figure 3A:
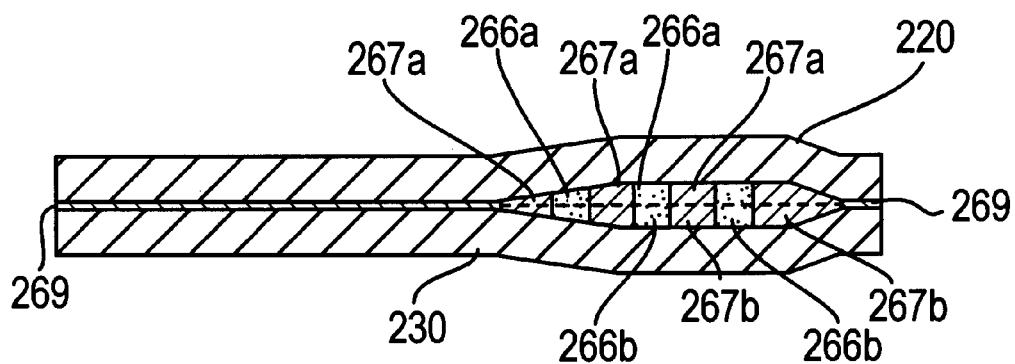
FIGS. 3(*a*) and 3(*b*) are explanatory views illustrating a process of forming a processing space in the gas sensor of FIG. 1.
Figure 3B:
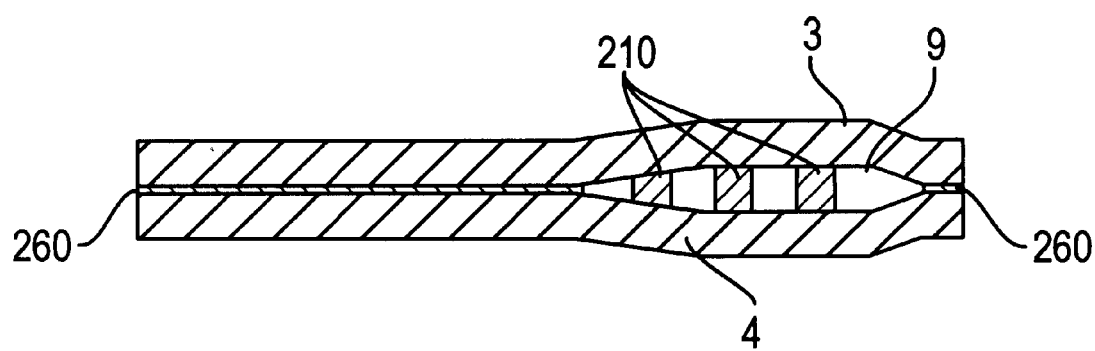

As shown in FIG. 3(b), in the first processing space 9 and the second processing space 10, supports 210 are formed in a scattered or staggered manner to thereby prevent the collapse of the spaces 9 and 10 during firing. The process of forming such a space structure will be described, taking the first processing space 9 as an example. As shown in FIG. 3(a), using a ceramic powder paste (for example, a paste of porous $Al_2O_3$ powder), support patterns 266a are formed on a ceramic green sheet 220 in a region for defining the first processing space 9. The ceramic green sheet 220 will be formed into the oxygen pumping element 3. Likewise, support patterns 266b are formed on a ceramic green sheet 230 in a region for defining the first processing space 9. The ceramic green sheet 230 will be formed into the oxygen concentration cell element 4. The support patterns 266a and 266b will be formed into supports 210. By using a paste material (for example, carbon paste) which will be burned or decomposed during firing, auxiliary support patterns 267a are formed on the ceramic green sheet 220 in a region for defining the first processing space 9 so as not to overlap the support patterns 266a. Likewise, auxiliary support patterns 267b are formed on a ceramic green sheet 230 in a region for defining the first processing space 9 so as not to overlap the support patterns 266b. Furthermore, using $Al_2O_3$ powder paste, an insulating layer pattern serving as a bonding coat 269 is formed between the ceramic green sheets 220 and 230 in a region other than the region for defining the first processing space 9. The thickness of the insulating layer pattern is made smaller than that of the supports 210. Although not shown in FIG. 3, by using a paste of porous $Al_2O_3$ powder, communicating-portion patterns are formed on both sides of the region for defining the first processing space 9. Once fired, the communicating-portion patterns will become the first gas passages 11.

The thus-prepared assembly of the ceramic green sheets 220 and 230 is subjected to firing. As a result, as shown in FIG. 3(b), the support patterns 266a and 266b are united into the supports 210 between the oxygen pumping element 3 and the oxygen concentration cell element 4, whereas the auxiliary patterns 267a and 267b disappear. The first processing space 9 is formed, while its size is maintained by the supports 210. As shown in FIG. 1(b), porous ceramic bodies form the first gas passages 11 on both widthwise sides of the first processing space 9. The oxygen concentration cell element 4 and the oxygen pumping element 3 are bonded together in a region other than the first processing space 9 by means of the bonding coat 269 serving as the insulating layer 260.

Figure 4A:
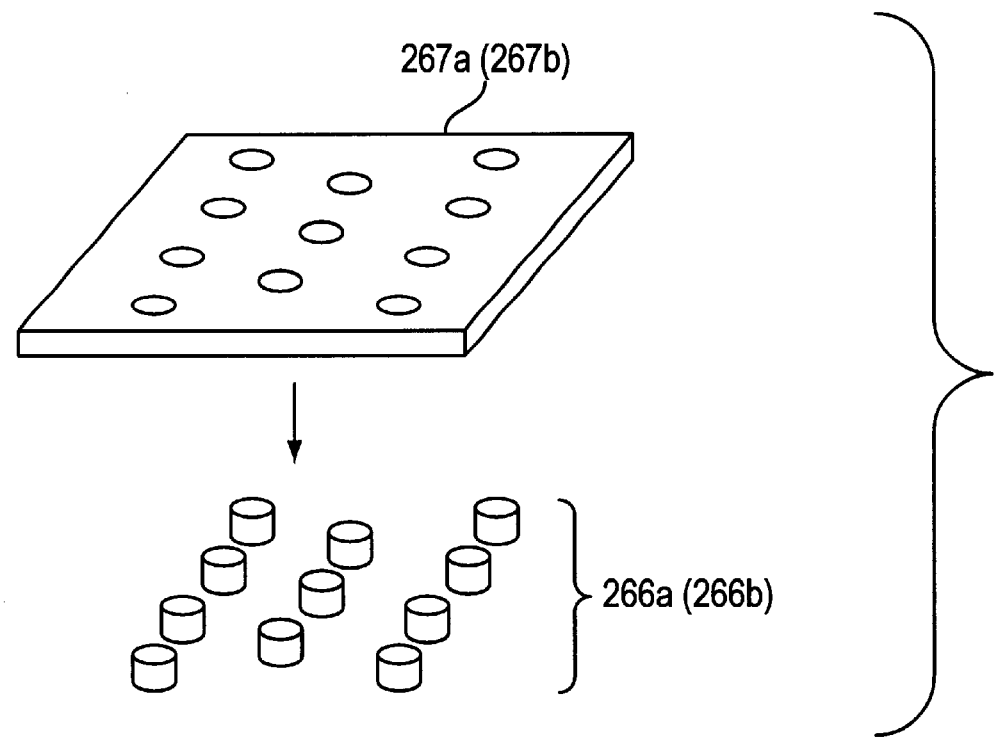
FIGS. 4(*a*) and 4(*b*) are explanatory views illustrating the process of forming the processing space in the gas sensor of FIG. 1.
Figure 4B:
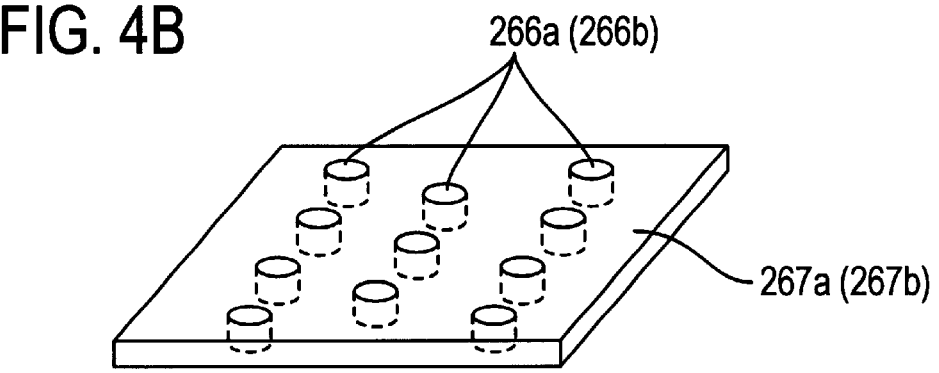

As shown in FIG. 4, the support patterns 266a (266b) and the auxiliary support pattern 267a (267b) are complementarily formed to thereby form a substantial plane. When the green sheets 220 and 230 are superposed on each other as shown in FIG. 3(a), the reinforcing effect of the auxiliary support patterns 267a and 267b prevents or suppresses the collapse of the support patterns 266a and 266b butting against each other. As exaggeratedly shown in FIG. 3(a), even when the bonding coat 269 is made considerably thinner than the total thickness of the support patterns 266a and 266b, the green sheets 220 and 230 can be bonded together by means of the interposed bonding coat 269. Because the green sheets 220 and 230 are flexible, the bonding can be established through slight flexure thereof. Thus, the green sheets 220 and 230 can be smoothly fired into a single unit.

Next, an embodiment of a gas sensor system using the above gas sensor 1 is described as follows.

Figure 5:
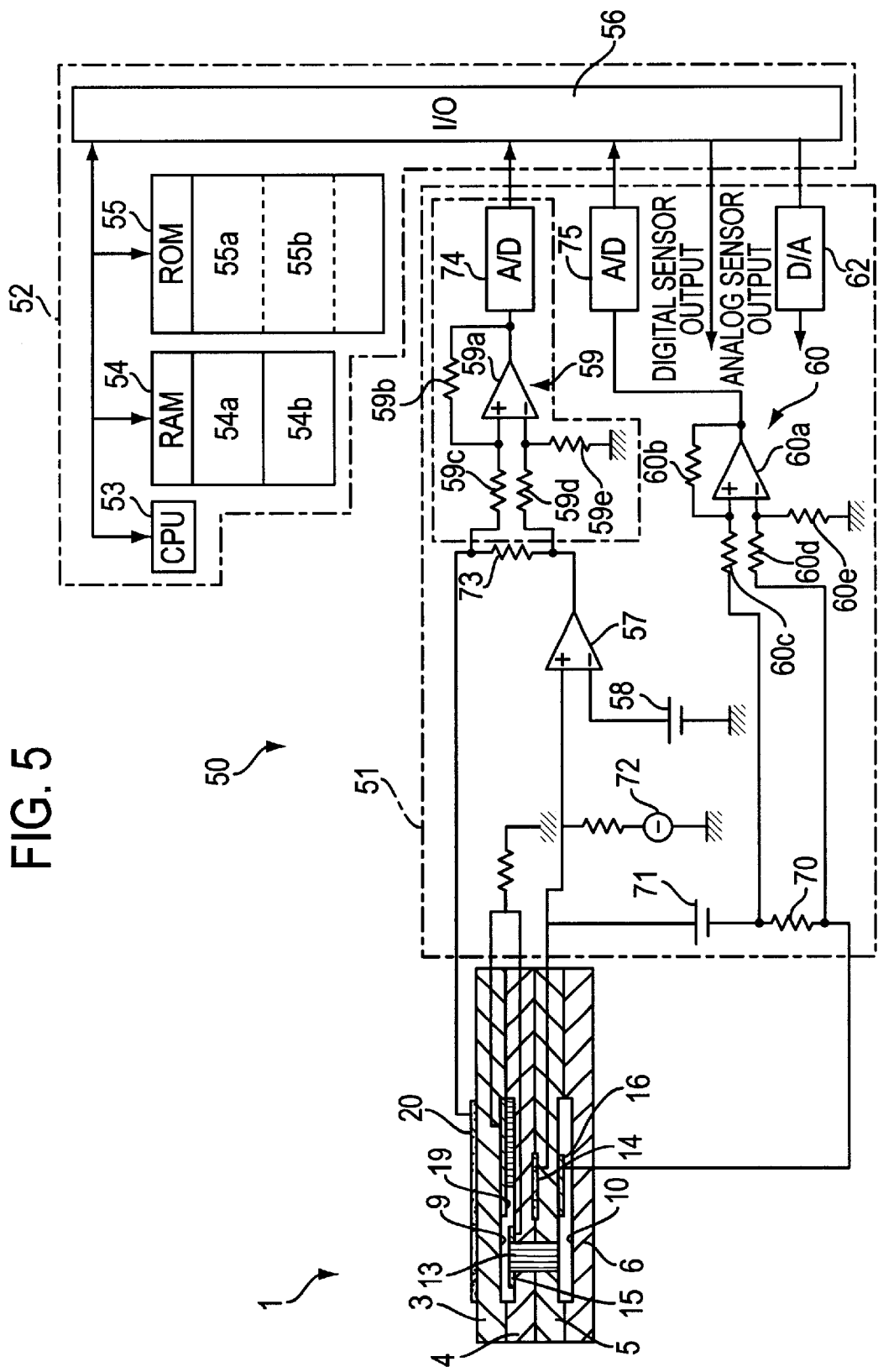
FIG. 5 is a block diagram showing a circuit configuration example of a gas sensor system using the gas sensor of FIG. 1.

FIG. 5 shows an example of an electrical block diagram of a gas sensor system (hereinafter referred to as the "sensor system") using the gas sensor 1. Specifically, the gas sensor system 50 includes the gas sensor 1, a microprocessor 52 and a peripheral circuit 51 for connecting the gas sensor 1 to the microprocessor 52. The microprocessor 52 is a main portion of an output conversion unit and includes an I/O port 56 serving as an input/output interface, a CPU 53, a RAM 54, a ROM 55, etc. The CPU 53, the RAM 54, the ROM 55, and the like are connected to the I/O port 56. The RAM 54 has a work area 54a for the CPU 53, and a storage area 54b for storing calculated values of component concentration. The ROM 55 contains a control program 55a and an HC concentration conversion table 55b. The control program 55a is used for controlling the gas sensor system 50 in computing a component concentration and in outputting the computed component concentration. The CPU 53 serves as concentration determination means, and determines a component concentration according to the control program 55a stored in the ROM 55.

In the gas sensor system 50, the gas sensor 1 operates in the following manner. The gas sensor 1 is heated to a predetermined working temperature by means of the first heater 2 and the second heater 8 (either of the heaters may be omitted). The working temperature is a temperature at which the $ZrO_2$ solid electrolyte forming elements 3 to 5 are activated. While the gas sensor 1 is heated at its working temperature, an exhaust gas, which is a measurement gas, is introduced into the first processing space 9 through the first gas passages 11. The oxygen concentration cell element 4 measures the oxygen concentration of the introduced measurement gas. Based on the measured oxygen concentration, the oxygen pumping element 3 pumps out oxygen from or pumps oxygen into the gas contained in the first processing space 9 such that the oxygen concentration detected by the oxygen concentration cell element 4 approaches a predetermined target value set within a range of $10^{-12}$ atm to $10^{-6}$ atm (preferably $10^{-11}$ atm to $10^{-9}$ atm), in other words, to a predetermined target value at which water vapor contained in the measurement gas is not substantially decomposed. Generally, the oxygen concentration of a measurement gas is higher than the above target value. In that case, the oxygen pumping element 3 operates so as to reduce the oxygen concentration of the first processing space 9. When the oxygen concentration measured by the oxygen concentration cell element 4 falls within the range of $10^{-12}$ atm to $10^{-6}$ atm, the corresponding concentration cell electromotive force of the oxygen concentration cell element 4 falls within the range of about 300 mV (corresponding to $10^{-5}$ atm)–600 mV (corresponding to $10^{-12}$ atm).

After reducing the oxygen concentration to a predetermined value, the gas contained in the first processing space 9 flows into the second processing space 10 through the second gas passage 13. Because the second electrode 16 has a higher oxidation related catalytic activity than the first electrode 15 toward a combustible gas component such as HC or the like, a combustible gas component of the gas contained in the second processing space 10 is burned while the second electrode 16 serves as an oxidation catalyst. Thus, oxygen is consumed. The oxygen concentration of the second processing space 10 varies according to oxygen consumption associated with the combustion, i.e., according to the concentration of a combustible gas component.

A constant-DC-voltage regulated power source 71 (FIG. 5) applies a constant voltage VC to the combustible gas component concentration detection element 5 via the electrodes 14 and 16. In the present embodiment, the polarity of the applied voltage VC is set such that the electrode exposed to the second processing space 10, i.e., the second electrode 16, becomes negative. The voltage VC is set to a value such that sufficient sensitivity is provided for reliably measuring a combustible gas component concentration, and such that the partial pressure of oxygen in the second processing space 10 does not drop to a value which would initiate decomposition of nitrogen oxides (NOx) contained in the measurement gas.

The output current of the combustible gas component concentration detection element 5 varies according to oxygen consumption associated with combustion of a combustible gas component contained in the gas introduced into the second processing space 10. Accordingly, the combustible gas component concentration of the measurement gas can be determined from the output current.

The circuit configuration and operation of the gas sensor system 50 will be described in more detail with reference to FIG. 5. In the gas sensor 1, the first electrode 15 of the oxygen concentration cell element 4 and the electrode 19 of the oxygen pumping element 3 exposed to the first processing space 9 are grounded through a resistor. The oxygen reference electrode 14 is connected to an input terminal of a differential amplifier 57. The constant-DC-voltage regulated power source 71 is connected to the combustible gas component concentration detection element 5 so as to apply the voltage VC to the element 5 via the electrodes 14 and 16 as described above. Thus, the electromotive force E of the oxygen concentration cell element 4 and the voltage VC are input in a superimposed manner to the above-described input terminal of the differential amplifier 57.

A power circuit 58 is connected to the other input terminal of the differential amplifier 57. The power circuit 58 outputs to the differential amplifier 57 a target electromotive force EC corresponding to a target oxygen concentration value (in actuality, the set voltage is (EC+VC)). The differential amplifier 57 amplifies the difference between the electromotive force E of the oxygen concentration cell element 4 and the target electromotive force EC, and inputs the amplified difference to the electrode 20 of the oxygen pumping element 3. Upon receiving the output from the differential amplifier 57, the oxygen pumping element 3 pumps oxygen out from or into the first processing space 9 so that the electromotive force E (corresponding to the oxygen concentration of the first processing space 9) approaches the target electromotive force EC. That is, the differential amplifier 57 serves as the oxygen pumping operation control means. The power circuit 58 may be configured such that the target electromotive force EC is fixedly set by a fixed voltage source or such that the target electromotive force EC can be variably set.

The oxygen concentration cell element 4 and the combustible gas component concentration detection element 5 share the common oxygen reference electrode 14. However, the constant-current regulated power source 72 causes a small DC current to continuously flow between the oxygen reference electrode 14 and the first electrode 15 (or the second electrode 16) in a direction such that oxygen is pumped into the oxygen reference electrode 14. That is, the oxygen reference electrode 14 serves as a self-generation type reference electrode. This feature causes pores formed in the oxygen reference electrode 14 to be always filled with a reference gas of near 100% oxygen. Thus, the electromotive force of the oxygen concentration cell element 4 and of the combustible gas component concentration detection element 5 is increased, thereby improving the measuring accuracy and the measuring sensitivity of the gas sensor 1.

The voltage applied by the constant-current regulated power source 72 is set such that the voltage becomes sufficiently smaller than the electromotive force E output from the oxygen concentration cell element 4, and such that the oxygen concentration of the oxygen reference electrode 14 becomes nearby 100%.

The output current of the combustible gas component concentration detection element 5 is detected, for example, as the difference between voltages measured at both ends of a resistor 70 for current measurement use. In the present embodiment, the output current signal undergoes voltage conversion effected by a differential amplifier 60 (including an operational amplifier 60a and peripheral resistors 60b to 60e), followed by analog-to-digital conversion effected by an A/D converter 75. The thus-obtained digital signal is input to the microprocessor 52.

Figures 6, 7:
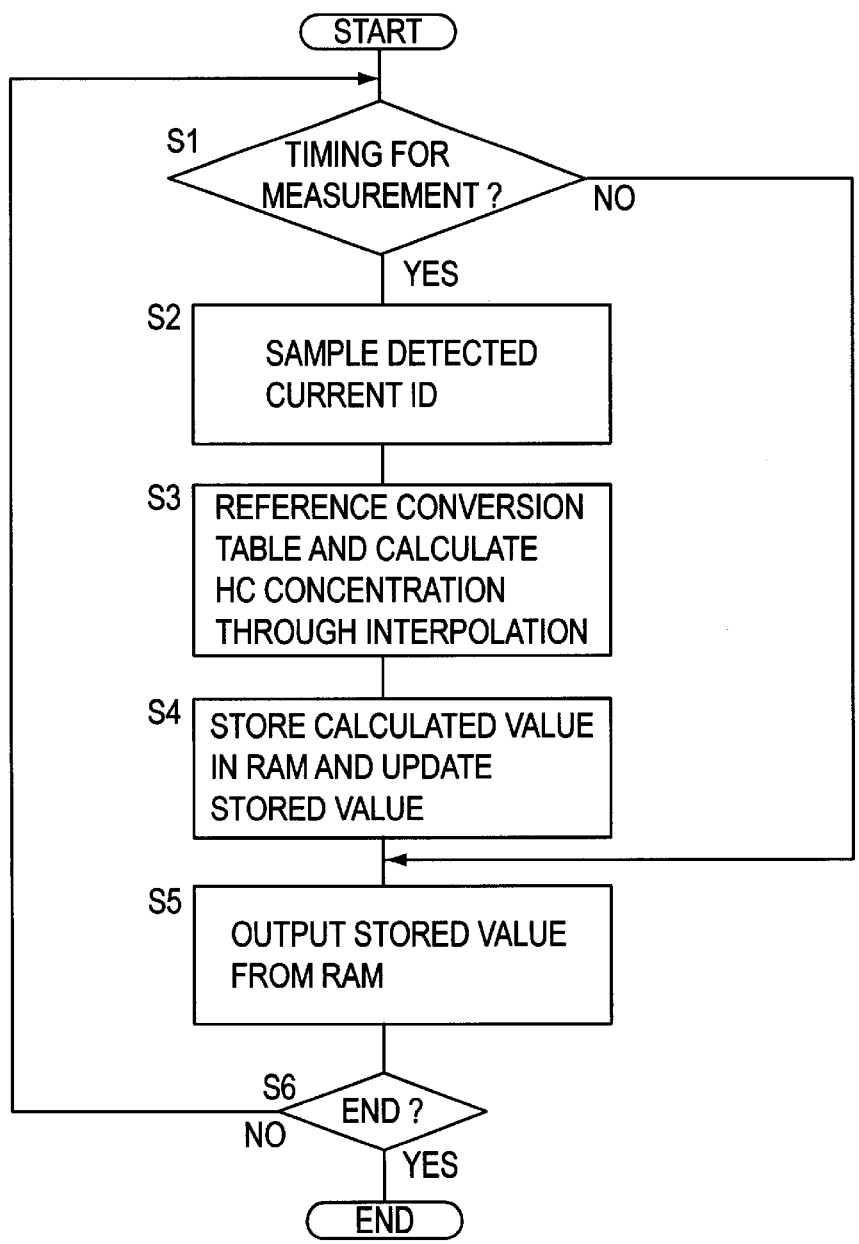
FIG. 6 is an explanatory diagram showing a contents example of a concentration conversion table.
FIG. 7 is a flow chart showing the process flow of a control program of the gas sensor system of FIG. 5.

The ROM 55 of the microprocessor 52 contains the control program 55a and the concentration conversion table 55b as described above. FIG. 6 shows an example of the contents of the concentration conversion table 55b. The table 55b contains values of detected current Id1, Id2, Id3, etc. of the combustible gas component concentration detection element 5 corresponding to values of combustible gas component concentration (for example, values of HC concentration) C1, C2, C3, etc. These values are previously determined based on experiments and the like. The CPU 53 (FIG. 5) carries out sensor output control as represented by the flowchart of FIG. 7 according to the control program 55a, using the RAM 54 as a work area.

Specifically, the measurement timing is metered using an unillustrated timer. In step S1, when the time for measurement is reached, processing proceeds to step S2. In step S2, the CPU 53 samples a detected current Id of the combustible gas component concentration detection element 5. In step S3, the CPU 53 calculates a combustible gas component concentration corresponding to the sampled value by interpolation while referencing the concentration conversion table 55b of FIG. 6. In step S4, the CPU 53 stores the calculated value into the calculated value storage area 54b of the RAM 54. The newly stored value overwrites a corresponding value stored previously in the area 54b. In step S5, the CPU 53 outputs the newly written calculated value from the I/O port 56 as information regarding the combustible gas component concentration of the measurement gas. The output may be either digital or analog. An analog output is obtained through digital-to-analog conversion effected by a D/A converter connected to the I/O port 56.

In the thus-configured operational gas sensor system 50, the oxygen concentration of the measurement gas introduced into the first processing space 9 is reduced to a predetermined value of $10^{-12}$ atm to $10^{-6}$ atm by operation of the oxygen pumping element 3. The thus-treated gas is introduced into the second processing space 10 and burned. The measured current Id of the combustible gas component concentration detection element 5 varies according to oxygen consumption associated with the combustion. Thus, the detected current Id is utilized as information regarding the combustible gas component concentration of a measurement gas. By operation of the oxygen pumping element 3, the oxygen concentration of the first processing space 9 is adjusted to a value at which water vapor contained the measurement gas is not substantially decomposed. Even when the decomposition reaction is initiated, the degree of the reaction is very small. Thus, an impairment in accuracy in measuring a combustible gas component concentration is effectively prevented which would otherwise result from combustion of hydrogen generated from the decomposition of water vapor.

Figure 8A:
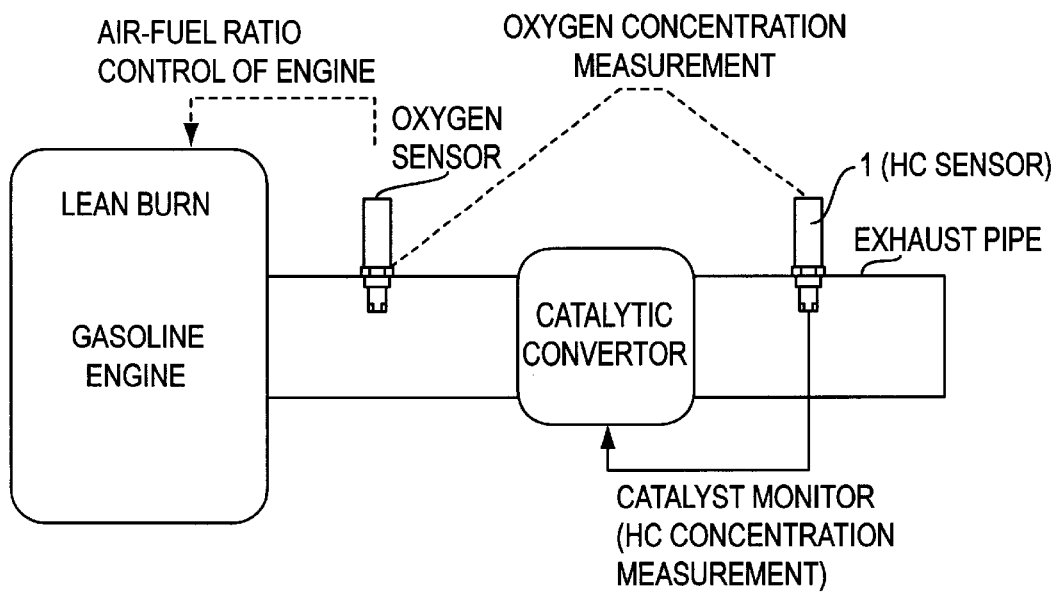
FIGS. 8(*a*) and 8(*b*) are schematic diagrams showing applications of the gas sensor of the present invention.
Figure 8B:
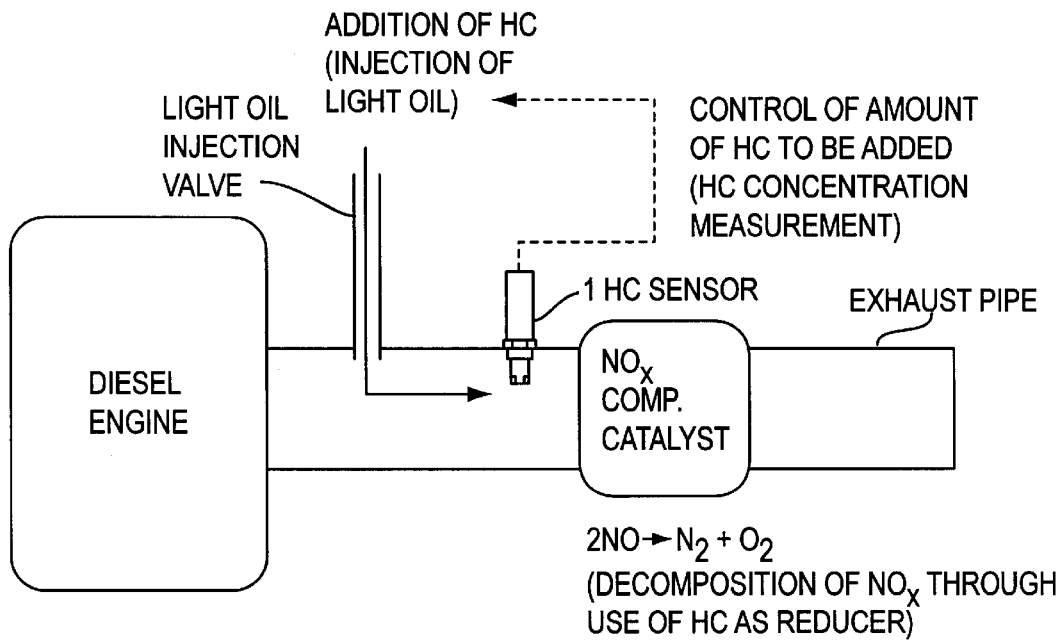

Next, applications of the gas sensor 1 or the gas sensor system 50 will be described. FIG. 8(*a*) schematically shows an exhaust gas purification system of a gasoline engine. An oxygen sensor, a three way catalytic converter, and the gas sensor of the present invention are attached onto an exhaust pipe in this order starting from the engine side. The oxygen sensor is used for air-fuel ratio control. The three way catalytic converter concurrently performs oxidation of HC and reduction of NOx to thereby purify the exhaust gas. The gas sensor 1 functions as an oxygen sensor for measuring the oxygen concentration of the purified exhaust gas, which is described below. The gas sensor 1 measures the HC concentration of the purified exhaust gas, for example, in order to judge whether the catalyst is deteriorated.

FIG. 8(*b*) schematically shows an exhaust gas purification system of a diesel engine. A light oil injection valve and an NOx decomposition catalyst are attached onto an exhaust pipe in this order starting from the engine side. The light oil injection valve is used for injecting light oil serving as an HC source into an exhaust gas. The NOx decomposition catalyst decomposes NOx into nitrogen and oxygen while using HC added through light oil injection as a reducer, thereby purifying the exhaust gas.

The gas sensor 1 of the present invention is disposed on the upstream side of the NOx decomposition catalyst and monitors the HC concentration of the light-oil-injected exhaust gas in order to feedback-control the amount of light oil to be injected into the exhaust gas.

In the gas sensor 1, the oxygen concentration cell element 4 and the combustible gas component concentration detection element 5 are each formed of a $ZrO_2$ solid electrolyte. In the case of the oxygen concentration cell element formed of a $ZrO_2$ solid electrolyte and configured such that one electrode is in contact with a gas to be measured, which gas contains oxygen and a combustible gas component, whereas the other electrode is in contact with a reference atmosphere having a constant oxygen concentration, its electromotive force varies abruptly when a gas composition falls outside a stoichiometric composition in which oxygen and a combustible gas component are present in a proper ratio so that they completely react with each other. When an ordinary gasoline engine or diesel engine is operated under lean-burn conditions, an exhaust gas emitted from the engine contains combustible gas components in a total concentration of about 0 to 1000 ppmC. A measurement gas having such a combustible gas component concentration is introduced into the first processing space 9, and the oxygen concentration of the introduced measurement gas is adjusted to $10^{-6}$ atm (preferably $10^{-9}$ atm) or lower as described above. As a result, the gas introduced into the second processing space 10 from the first processing space 9 has a stoichiometric composition or a composition shifted slightly toward a rich condition. Thus, the output electromotive force of the combustible gas component concentration detection element 5 is increased, thereby improving the sensitivity of the gas sensor 1.

In the gas sensor 1, as shown in FIG. 1, a porous metal layer 17 other than the second electrode 16 may be formed on the shield member 6, which is disposed opposite the partition wall 12 with respect to the second processing space 10 so as to be exposed to the second processing space 10. The porous metal layer 17 may be formed of a metal, e.g., Pt, having a higher catalytic activity with respect to combustion of a combustible gas component than the electrodes 15 and 19. The thus-formed porous metal layer 17 serves as an oxidation catalyst section as well as the second electrode 16. This feature enhances the efficiency of burning a combustible gas component in the second processing space 10, thereby improving the sensitivity of the gas sensor 1. When the porous metal layer 17 has a sufficiently high catalytic activity, the second electrode 16 may be formed of a material having a relatively low catalytic activity, for example, a Pt—Au alloy, as in the case of the electrodes 15 and 19.

In the gas sensor system 50, after the oxygen concentration of the first processing space 9 is reduced to a predetermined value, the combustible gas component concentration of the second processing space 10 is measured. Accordingly, the detected output of the combustible gas component concentration detection element 5 is substantially less affected by the oxygen content of the measurement gas. However, when the detected output of the combustible gas component concentration detection element 5 somewhat varies depending on the oxygen concentration of the measurement gas, the detected output may be corrected for the oxygen concentration, thereby further improving accuracy in measuring a combustible gas component concentration.

In this case, the oxygen concentration of a measurement gas may be measured using a separately provided oxygen sensor. However, because the current flowing through the oxygen pumping element 3, i.e., the oxygen pumping current Ip, varies substantially linearly with the oxygen concentration of a measurement gas, information regarding the oxygen concentration of a measurement gas may be obtained from the pumping current Ip. This provides the advantage of dispensing with the need for another oxygen sensor.

Specifically, as shown in FIG. 5, the resistor 73 used or current measurement is provided in an output path of the differential amplifier 57. The pumping current Ip is detected by means of a differential amplifier 59 (including an operational amplifier 59a and peripheral resistors 59b to 59e) in the form of the difference between voltages as measured at both ends of the resistor 73. The thus-detected pumping current Ip is input to the microprocessor 52 via an A/D converter 74. As shown in FIG. 9, the concentration conversion table 55b of the ROM 55 assumes the form of a two-dimensional table and contains groups of values of combustible gas component concentration (for example, values of HC concentration) corresponding to values of detected current Id1, Id2, Id3, etc. of the combustible gas component concentration detection element 5. The groups of values of combustible gas component concentration are associated with various values of pumping current Ip (i.e., values of oxygen concentration). A combustible gas component concentration corresponding to a combination of a measured pumping current Ip and a measured output current Id is calculated with reference to the concentration conversion table 55b using two-dimensional interpolation. The thus-obtained value is output as a corrected combustible gas component concentration. In this case, the contents of the concentration conversion table 55b serve as information regarding the relationship between the output current and a combustible gas component concentration. The CPU 53 of the microprocessor 52 serves as the correction means.

In FIG. 5, the polarity of the output current of the combustible gas component concentration detection element 5 (i.e., the current flowing between the second electrode 16 and the oxygen reference electrode 14) may become opposite that of the above voltage VC, depending on the relationship between the absolute value and polarity of the electromotive force of the oxygen concentration cell element 4 and the oxygen concentration within the second processing space 10. This phenomenon will be described with reference to FIG. 22. The oxygen concentration within the second processing space 10 is always lower than that of the oxygen reference electrode 14. Thus, with the absolute value of voltage of the power source 71 taken as VC and the absolute value of the oxygen concentration cell electromotive force of the combustible gas component concentration detection element 5 taken as Ea, Id varies with (VC-Ea). When VC is equal to Ea, Id becomes substantially zero. When the combustible gas component concentration of a gas flowing into the second processing space 10 increases with a resultant increase in the amount of oxygen to be consumed by combustion, the oxygen concentration cell electromotive force Ea increases. Id flows in a direction toward the oxygen reference electrode 14 (oxygen flows to the second electrode 16; the polarity of Id is defined as negative). By contrast, when the combustible gas component concentration decreases, the oxygen concentration cell electromotive force Ea decreases. Id flows in a direction toward the second electrode 16 (oxygen flows to the oxygen reference electrode 14; the polarity of Id is defined as being positive).

In this case, the oxygen concentration cell element 4 and the combustible gas component concentration detection element 5 share the oxygen reference electrode 14, which is a self-generation type reference electrode. Accordingly, when Id flows in the negative direction and its absolute value is excessively high (i.e., with a negative limit value taken as —Idn (Idn>0), Id<−Idn), a large amount of oxygen flows out from the oxygen reference electrode 14 into the second electrode 16. Thus, the oxygen reference electrode 14 fails to maintain an oxygen concentration required for serving as an oxygen reference electrode. As a result, the oxygen concentration cell element 4 fails to properly operate, and consequently control of the oxygen concentration within the first processing space 9 is disabled, resulting in impaired detection accuracy of the sensor 1.

Meanwhile, when the concentration of hydrocarbon or a like component in exhaust gas from an internal combustion engine is to be detected, a fuel cut or a like operation (performed, for example, in order to prevent overheating of the catalyst or to save fuel during deceleration with a throttle valve fully closed or in a like mode) may cause an D excessive increase in the oxygen concentration of the exhaust gas to be measured. In this case, Id flows in the positive direction and its absolute value is excessively high (i.e., with a positive limit value taken as Idp (Idp>0), Id>Idp), and a large amount of oxygen flows into the oxygen reference electrode 14. Thus, the internal pressure of the oxygen reference electrode 14 becomes excessively large, causing a problem such as breakage of the electrode.

Figure 22:
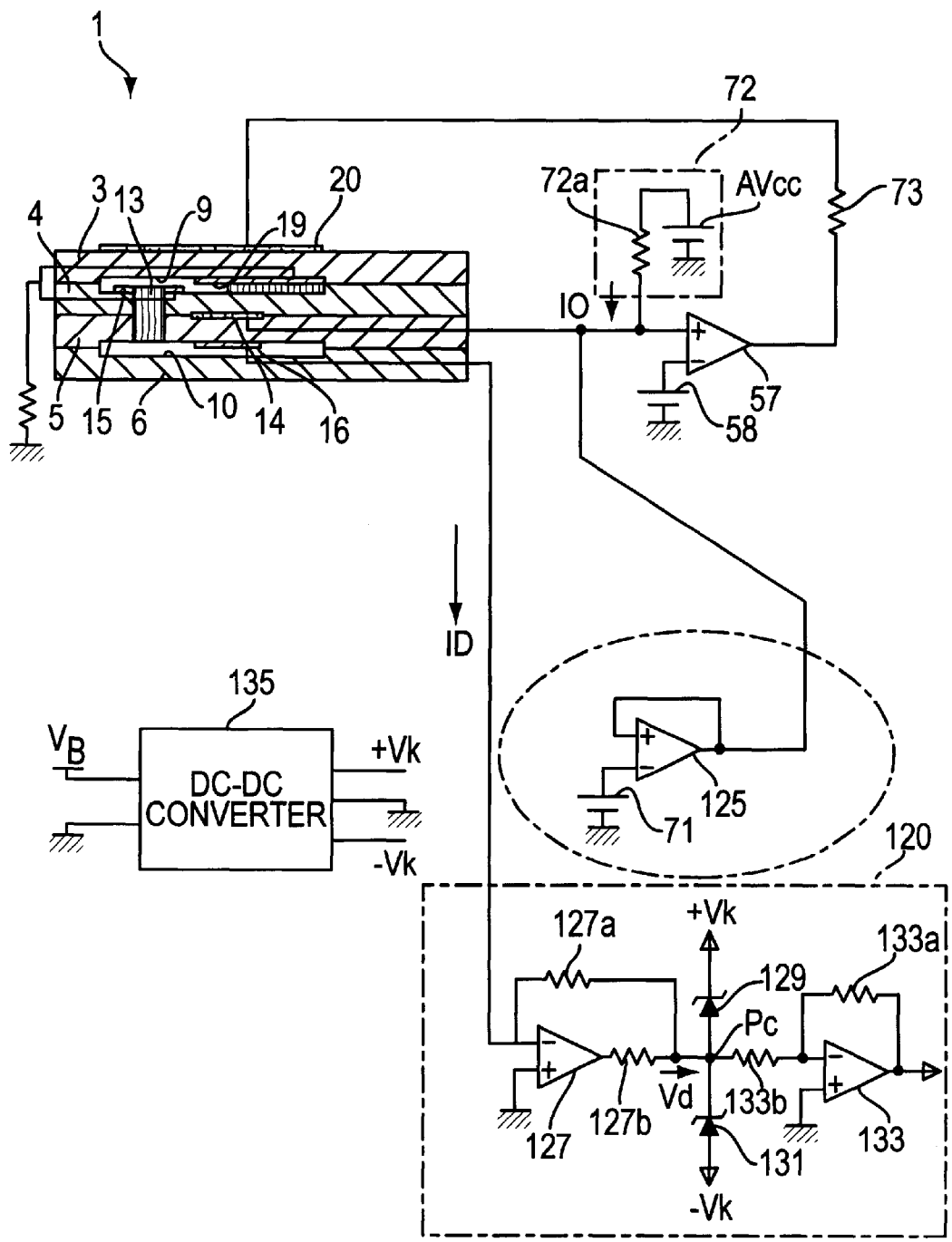
FIG. 22 is a circuit diagram showing an example of a sensor peripheral circuit having a current limit circuit.
Figure 23:
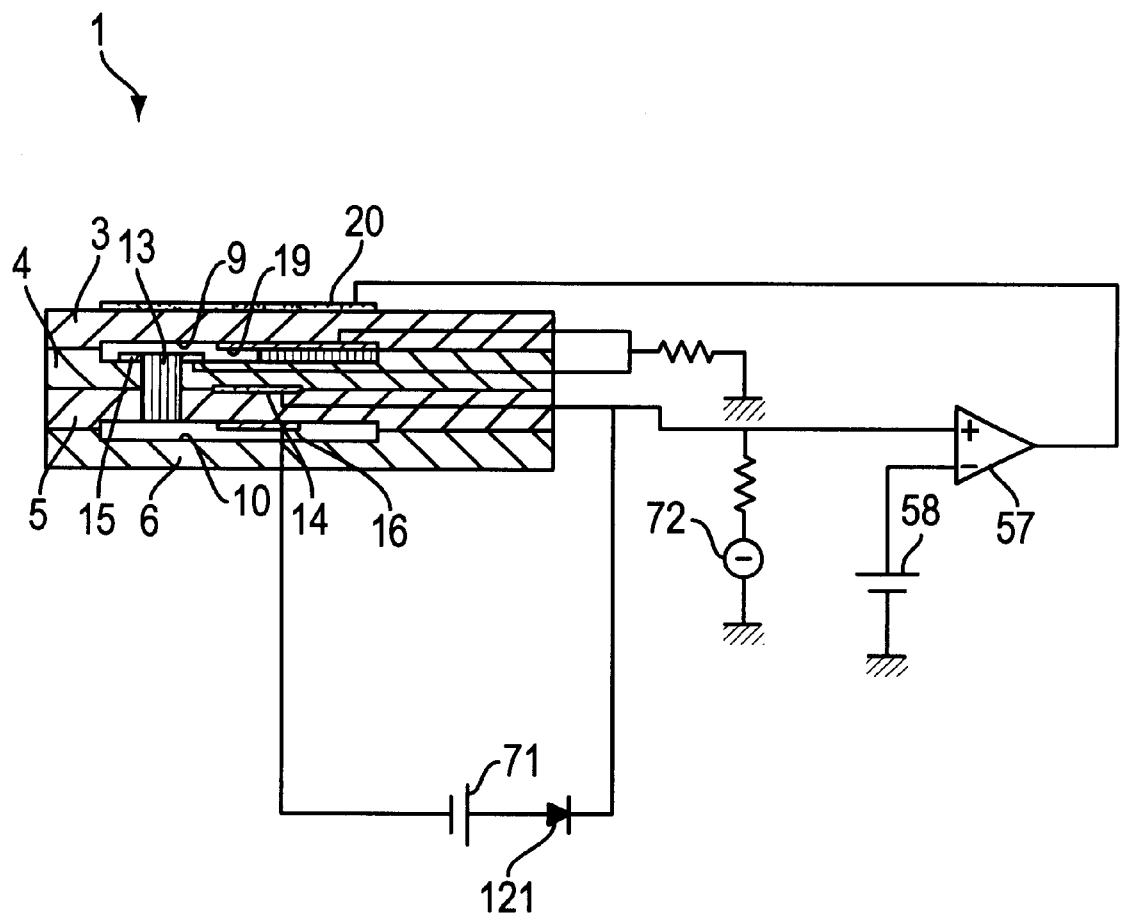
FIG. 23 is a circuit diagram showing the use of a diode to simplify the current limit circuit.

In order to avoid such problems, a current limit circuit is advantageously provided in a conductive passage extending between the combustible gas component concentration detection element 5 and the constant-DC-voltage regulated power source 71. The current limit circuit hinders a flow of Id falling outside the range "—Idn<Id<Idp." FIG. 22 shows an example of the current limit circuit (the same features as those of the circuit of FIG. 5 are denoted by common reference numerals, and their detailed description is omitted). In FIG. 22, the constant voltage VC from the constant-DC-voltage regulated power source 71 is applied via a voltage follower 125 such that the oxygen reference electrode 14 becomes positive. Also, a current limit circuit 120 is provided on a current output passage extending from the second electrode 16. The constant-current regulated power source 72 applies the source voltage AVcc to the oxygen concentration cell element 4 via a resistor 72a that has a sufficiently large resistance as compared to the internal resistance of the oxygen concentration cell element 4 at the sensor operation temperature (for example, 1000 to 5000 times the internal resistance). As a result, a substantially constant small current Io is applied to the oxygen concentration cell element 4 in a direction such that oxygen is pumped out from the first processing space 9 into the oxygen reference electrode 14.

In the current limit circuit 120, the current Id from the second electrode 16 is converted to a corresponding output voltage Vd by an operational amplifier 127. The operational amplifier 127, together with resistors 127a and 127b, constitute a current-voltage conversion circuit (hereinafter, referred to as the current-voltage conversion circuit 127). The output voltage Vd is supplied to a voltage control point Pc. Zener diodes 129 and 131 are connected to the voltage control point Pc. Voltages Vk and −Vk (Vk>0) are applied to the Zener diodes 129 and 131, respectively. The Zener diodes 129 and 131 are selected so as to have Zener voltages (Vk+Vdn) and (Vk+Vdp) corresponding to current limits Idn and Idp, respectively. The voltages Vk and −Vk are generated by conversion of a car battery voltage Vb by means of a DC—DC converter 135.

When a voltage at the control point PC is about to exceed Vdp (i.e., when the current Id is about to exceed Idp), the Zener diode 131 becomes conductive. Similarly, when the voltage at the control point PC is about to drop below −Vdn, the Zener diode 129 becomes conductive. Thus, the current Id is controlled such that −Idn<Id<Idp. The operational amplifier 133, together with resistors 133a and 133b, constitute an inversion amplifier for outputting Vd.

When prevention of Id<−Idn alone suffices, the bidirectional current limit circuit 120 may be replaced with a unidirectional current limit circuit. When prevention of Id<0 (i.e., prevention of leakage of oxygen from the oxygen reference electrode 14 to the second electrode 16) alone suffices, the current limit circuit 120 may be replaced with a diode 121 for shutting off current in the corresponding direction.

Figure 24:
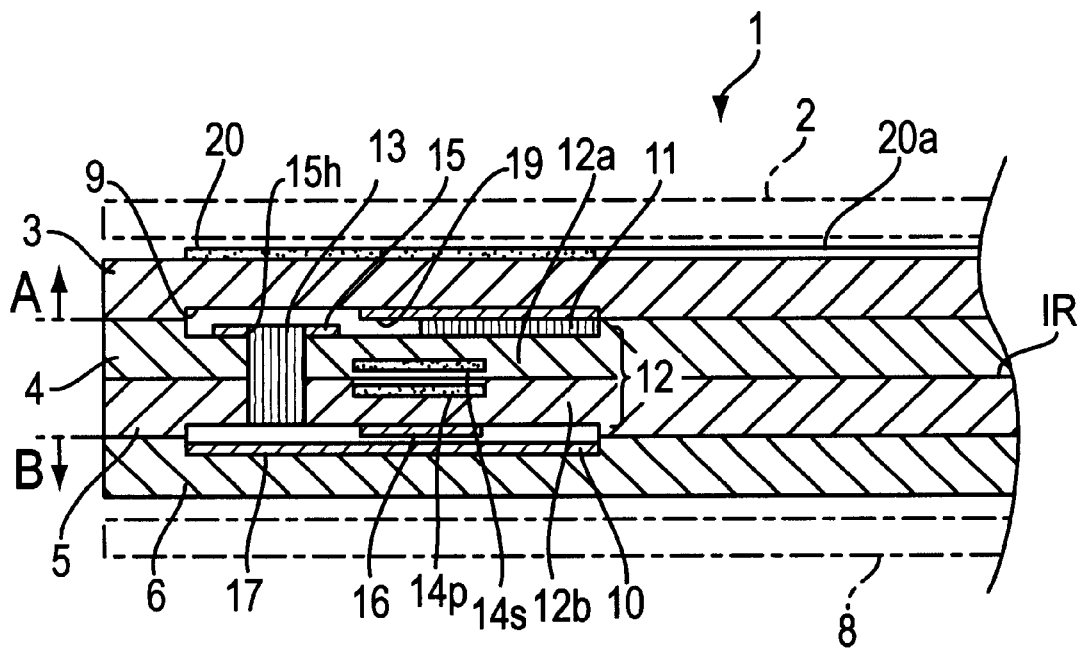
FIG. 24 is a sectional view showing a modification of the sensor of FIG. 1.
Figure 25:
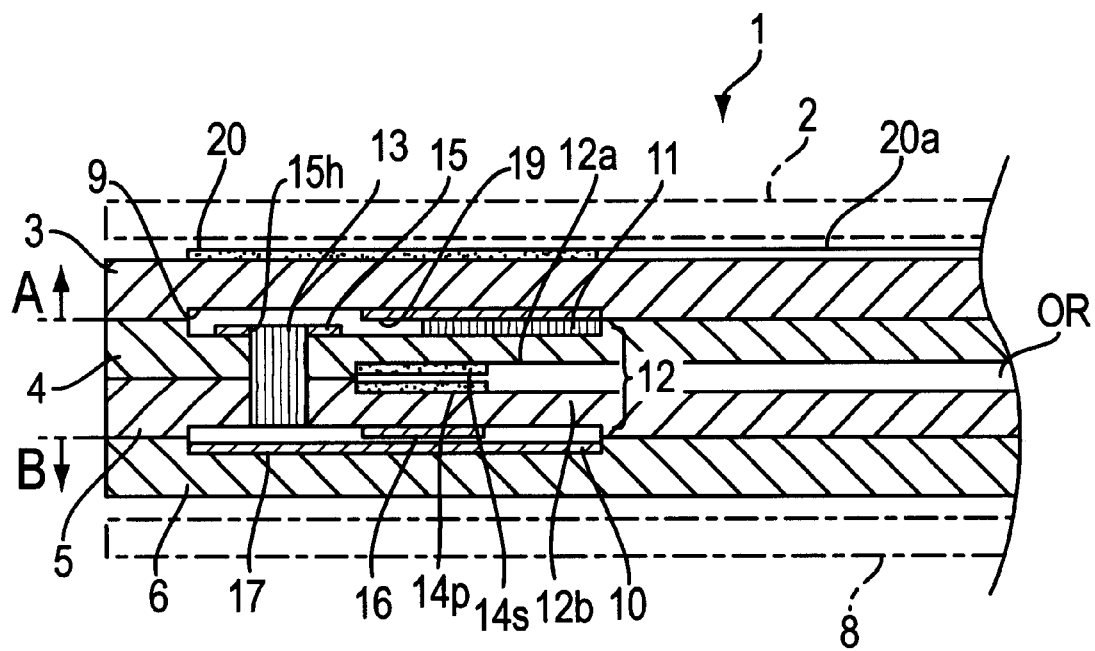
FIG. 25 is a sectional view showing another modification of the sensor of FIG. 1.

Also, insofar as the reference potential of the oxygen reference electrode 14 (or the oxygen concentration of the gas held in the voids of the oxygen reference electrode 14) is maintained in a range that guarantees proper measurement, the polarity of the applied VC may be set opposite that of the above-described case, i.e., such that oxygen is pumped from the oxygen reference electrode 14 into the second processing space 10. The oxygen reference electrode 14 is a self-generation type electrode embedded in the partition wall 12. However, for example, as shown in FIG. 25, a reference space OR, into which the atmosphere serving as a reference gas is introduced via an atmosphere communication portion, is provided in the partition wall 12. On the inner surfaces of the reference space OR an oxygen reference electrode 14s may be provided associated with the oxygen concentration cell element 3, and an oxygen reference electrode 14p may be provided associated with the combustible gas component concentration detection element 5. Alternatively, as shown in FIG. 24, self-generation type oxygen reference electrodes 14s and 14p corresponding to the oxygen concentration cell element 3 and the combustible gas component concentration detection element 5, respectively, may be embedded in the wall partition 12 such that the electrodes 14s and 14p are isolated from each other by means of, for example, an insulating layer IR mainly composed of alumina or the like. In these cases, the polarity of the applied Vc may be set such that oxygen is pumped out from the second processing space 10 into the oxygen reference electrode 14 or such that oxygen is pumped out from the oxygen reference electrode 14 into the second processing space 10.

Figure 26A:
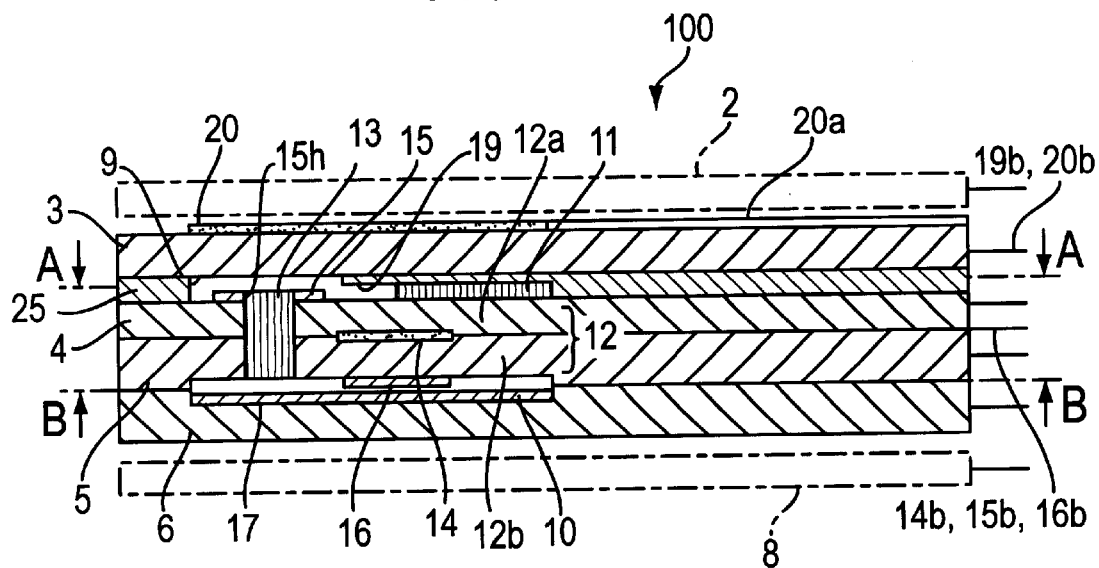
FIG. 26(*a*) is a sectional view showing a gas sensor according to a second embodiment of the present invention.
Figure 26B:
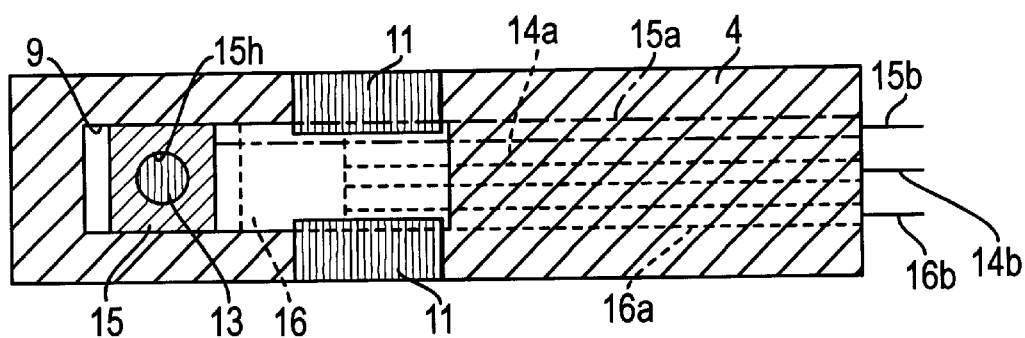
Figure 26C:
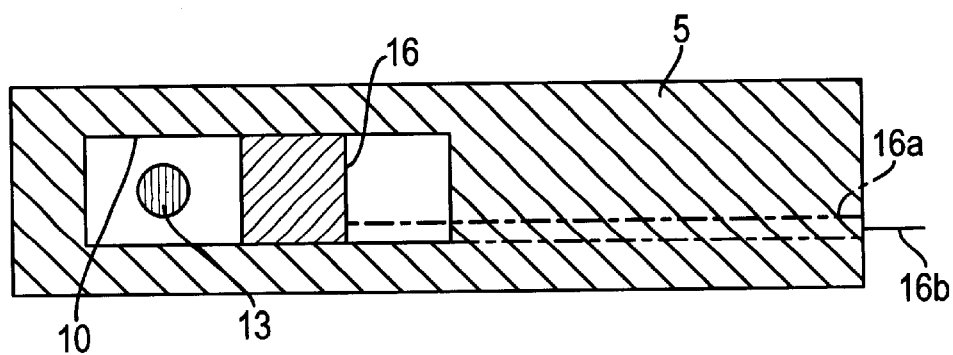
Figure 27:
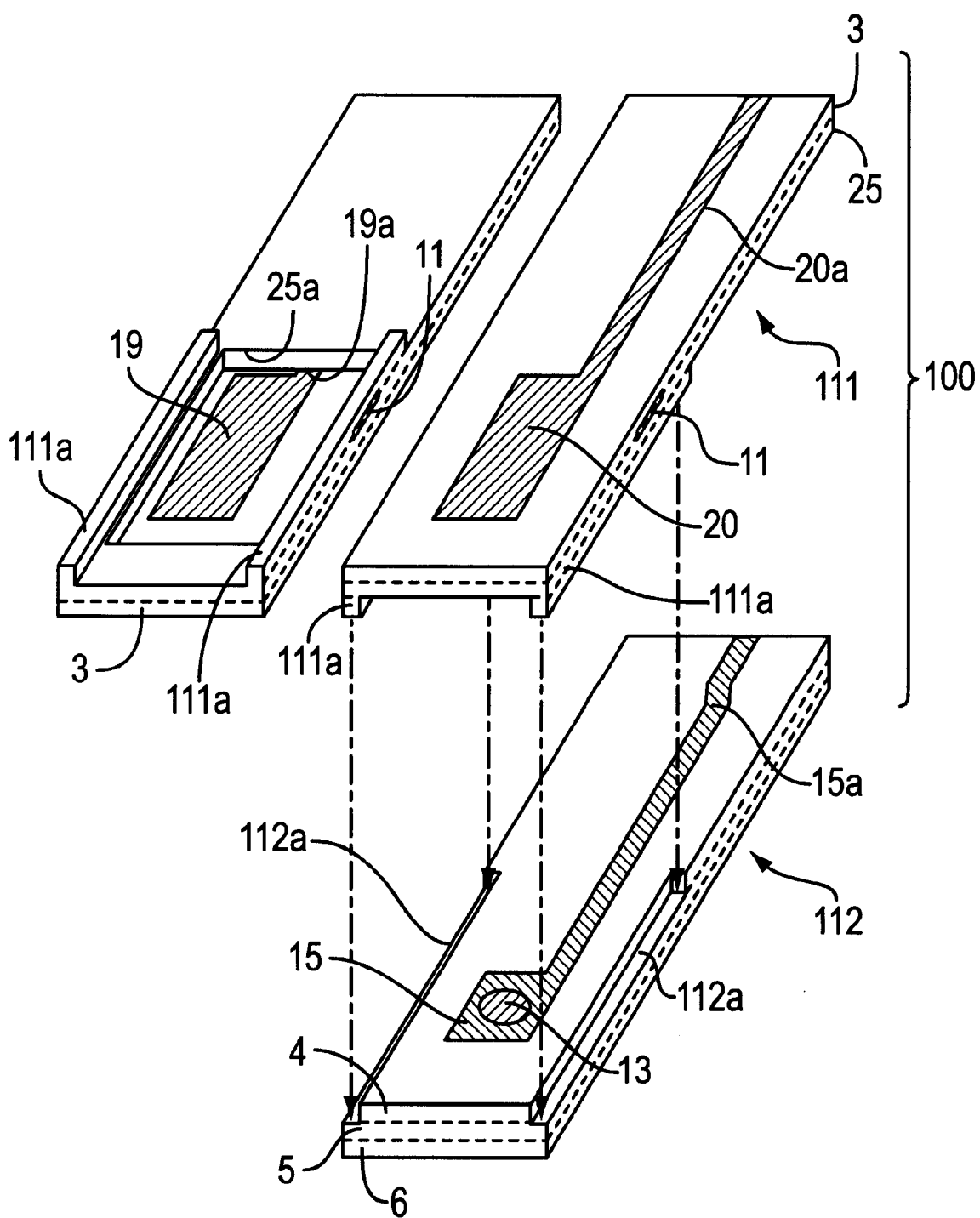
FIG. 27 is an exploded perspective view showing the gas sensor of FIG. 26 and a rear view of a pumping cell unit.

Second Embodiment:

A gas sensor 100 of FIG. 26 shows a modification of the gas sensor shown in FIG. 1. Portions identical to those of the gas sensor 1 are denoted by the same symbols, and detailed descriptions therefor are omitted. In the following description, the difference between the gas sensor 100 and the gas sensor 1 will mainly be described. In the gas sensor 100, a spacer 25 similar to that shown in FIG. 3(b) is integrated with the first pumping element 3. Thus, the first processing space is formed by means of a space 25a of the spacer section 25 (FIG. 27). As shown in FIG. 27, the entire sensor 100 is divided in two at an interface between the spacer 25 and the oxygen concentration cell element 4. Thus, as shown in FIG. 26, a pumping cell unit 111 is formed including the first pumping element 3, and a sensor cell unit 112 is formed including the oxygen concentration cell element 4 (oxygen concentration detection element), the second processing space (FIG. 26), the combustible gas component concentration detection element 5 and the shield member 6. The oxygen pumping element 3, the oxygen concentration cell element 4 and the spacer 25 form a main portion of the first processing space, while the combustible gas component concentration detection element 5 and the shield member 6 form a main portion of the second processing space.

As shown in FIG. 27, the pumping cell unit ill and the sensor cell unit 112 are superposed on each other such that the third electrode 19 faces the first electrode 15, and are joined and integrated together using a bonding material such as glass applied to their respective superposition surfaces. Furthermore, at the widthwise opposite sides of the superposition surface of the pumping cell unit 111 are formed rib-shaped fitting projections 111a (pump-cell-side fitting portion) that extend along the edges of the pumping cell unit 111. The fitting portions 111a are fitted into the fitting depressions 112a (sensor-cell-side fitting portions) formed on the sensor cell unit 112 at corresponding portions for positioning during superposition.

Figure 28A:
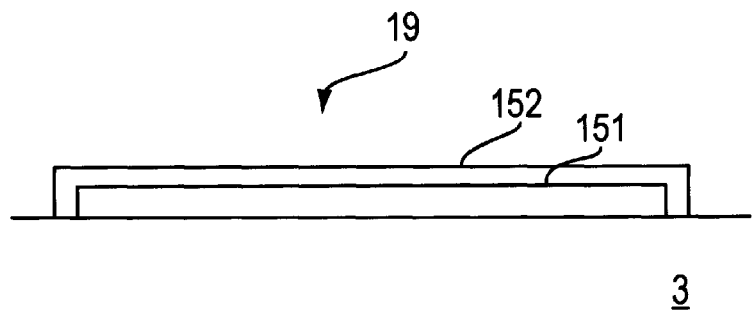
FIGS. 28(*a*), 28(*b*) and 28(*c*) are schematic views showing structures of the third electrode of the gas sensor of FIG. 26.

As shown in FIG. 28(a), the third electrode 19 has a two-layer structure composed of a porous main electrode layer 151 and a porous surface electrode layer 152 that forms a surface portion of the third electrode 19. The main electrode layer 151 is formed of Pt or a Pt—Au alloy (in the present embodiment, substantially the entire portion is formed of Pt). The surface electrode layer 152 is formed of an Au-containing metal that contains Au as a main component (in the present embodiment, substantially the entire portion is formed of Au). The first electrode 15 shown in FIG. 27 is formed of a porous metal such as porous Pt or a porous Pt—Au alloy (Au content: not greater than 1 wt. %) (in the present embodiment, substantially the entire portion is formed of Pt) as in the case of the other electrodes.

Because the surface of the porous main electrode layer 151 formed of Pt, which has a high activity of desorbing oxygen molecules, is covered with the porous surface electrode layer 152 formed of Au which has a low catalytic activity for combustion of a combustible gas component, the catalytic activity for combustion of the combustible gas component within the first processing space can be decreased, while the activity of desorbing oxygen molecules is maintained at a sufficient level. Thus, a loss of a combustible gas component such as HC to be detected can be prevented such that the sensor sensitivity can be increased. In the case where substantially the entire portion of the main electrode layer 151 is formed of Pt and substantially the entire portion of the surface electrode layer 152 is formed of Au, the value of $\{WAu/(WPt+WAu)\} \times 100$ preferably falls within the range of 2–20 wt. %, where WPt is the Pt content by weight of the third electrode 19, and WAu is the Au content by weight of the third electrode 19. When this value is less than 2 wt. %, the combustion catalytic activity of the third electrode 19 cannot be sufficiently decreased, with a possible result that the sensitivity of the sensor decreases. By contrast, when the value exceeds 20 wt. %, the catalytic activity of the third electrode 19 for desorption and recombination of oxygen molecules decreases excessively, with a possible result that the function of the oxygen pumping element 3 becomes insufficient. More preferably, the value falls within the range of 3–10 wt. %.

Figure 28B:
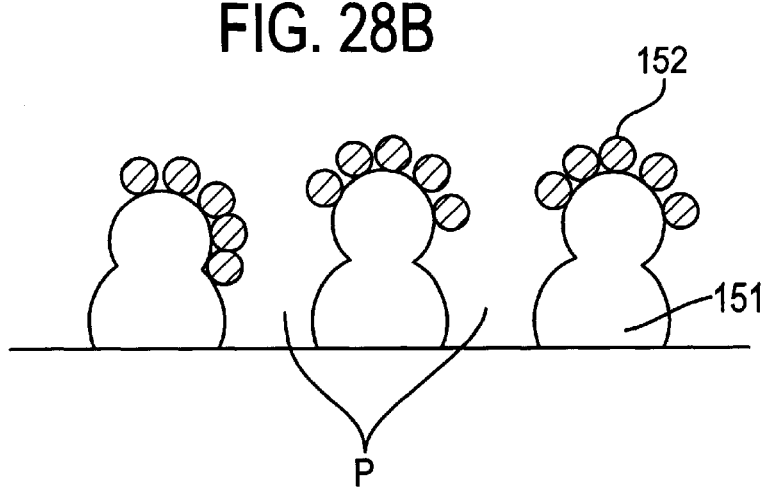
Figure 28C:
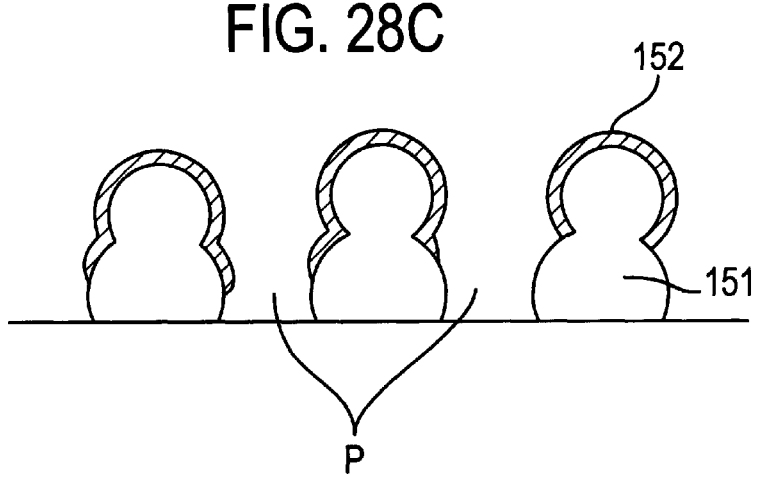

A method shown in FIG. 28(b) may be used to form the surface electrode layer 152 on the main electrode layer 151. That is, a paste containing particles of a material for the surface electrode layer 152 is applied onto the fired main electrode layer 151, and is then fired at a temperature lower than that used for the firing of the main electrode layer 151. Alternatively, as shown in FIG. 28(c), the surface electrode layer 152 may be formed using vapor-phase film formation such as vacuum deposition or sputtering. As shown in FIGS. 28(b) and (c), because many voids are formed in the porous main electrode layer 151 in a complex manner, the surface electrode layer 152 may not be formed such that its material fails to enter deeply into the voids P. In this case, parts of the main electrode layer 151 are not covered by the surface electrode layer 152 and remain exposed. However, because such exposed portions exhibit a strong catalytic activity for desorption and recombination of oxygen molecules, the formation of such exposed portions is rather preferable in terms of securing the function of the oxygen pumping element.

An example process for manufacturing the pumping cell unit 111 and the sensor cell unit 112 shown in FIGS. 26 and 27 will be described with reference to FIGS. 29 and 30.

Figure 29:
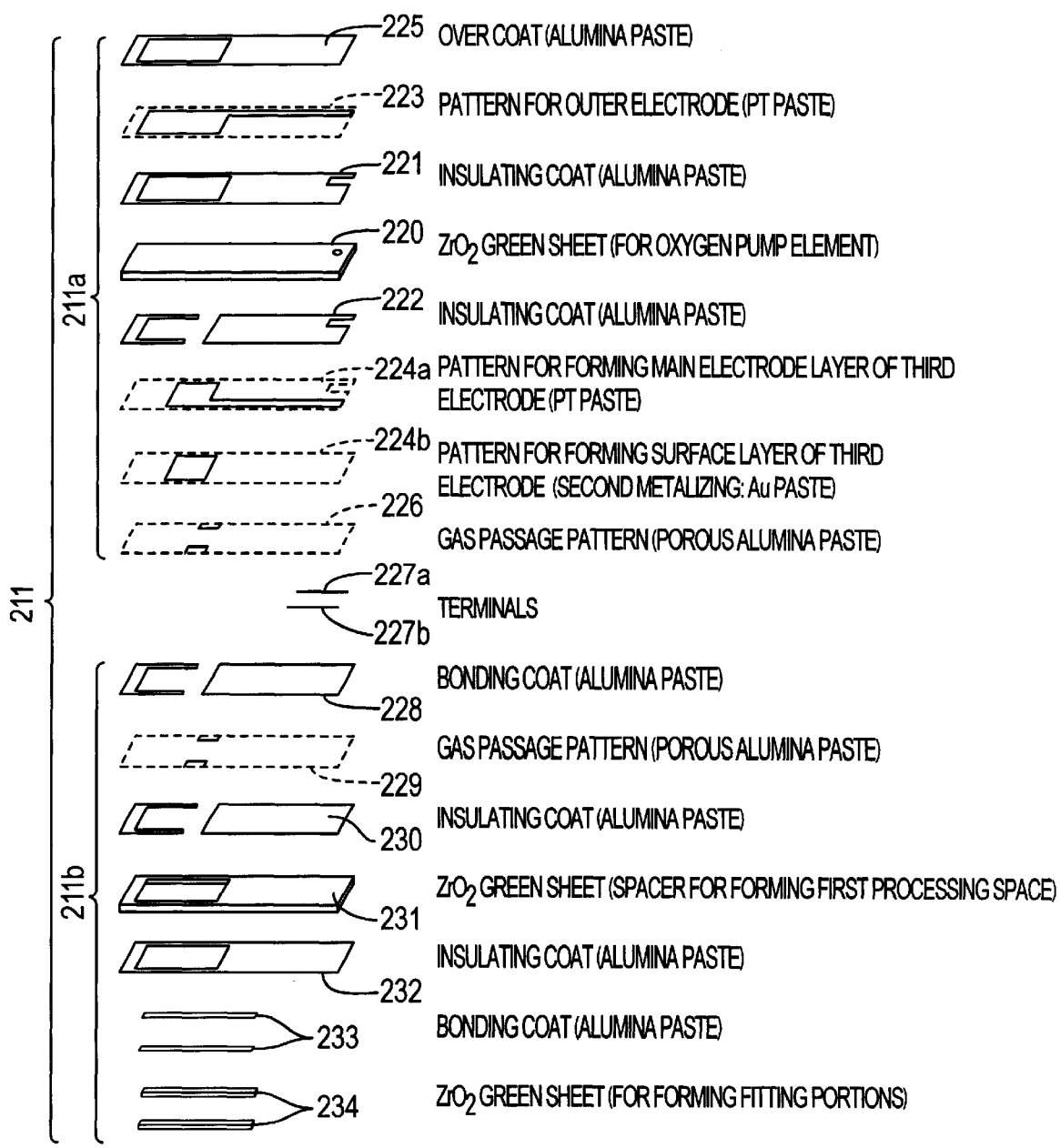
FIG. 29 is an exploded perspective view showing a method of manufacturing the pumping cell unit of the gas sensor of FIG. 26.

FIG. 29 shows a laminate structure of a first unfired assembly 211 used for manufacturing the pumping cell unit 111. The first unfired assembly 211 includes a first portion 211a and a second portion 211b. The first portion 211a is mainly composed of a $ZrO_2$ green sheet (hereinafter referred to as a green sheet) 220, which will become the first pumping element 3. The second portion 211b is mainly composed of a green sheet 231, which will serve as the spacer 25. The green sheet is formed by sheeting a kneaded mixture of a $ZrO_2$ powder, a forming aid such as an organic binder and an organic solvent.

In the first portion 211a, by using an $Al_2O_3$ paste or the like, insulating coats (insulating layer patterns) 221 and 222 for insulating the leads 20a and 19a from the first pumping element 3 are formed on the corresponding surfaces of the green sheet 220 in regions other than those corresponding to the electrodes 20 and 19 (FIG. 26). After the insulating coats 221 and 222 are formed, electrode patterns 223 and 224a for forming the electrodes 20 and 19 (only a main electrode layer 151 for the electrode 19 (FIG. 28)) and the leads 20a and 19a are formed by printing using a Pt paste or the like. A pattern 226 of porous alumina paste or the like, which will serve as a first gas passage 11, is provided on the pattern 224b. A protective over coat 225 is formed on the electrode pattern 223, which will serve as the outer electrode 20, using an $Al_2O_3$ paste or the like.

In the second portion 211b, insulating coats 230 and 232 are formed on the corresponding surfaces of the green sheet 231 in a manner similar to that used for the first portion 211a. A pattern 229, which will serve as a first gas passage 11, is formed on the insulating coat 230 using an $Al_2O_3$ paste. Green sheets 234, which will serve as fitting projections 111a, are bonded onto the insulating coat 232 using bonding coats 233 (formed from alumina paste).

The first portion 211a and the second portion 211b are bonded together using a bonding coat 228, while end portions of Pt—Rh alloy wires 227a and 227b, which will serve as terminals of the electrodes 20 and 19, are sandwiched between the portions 211a and 211b. The thus-obtained first unfired assembly 211 is fired to obtain a pumping cell unit in which a surface electrode layer 152 (FIG. 28) of the third electrode 19 is not yet formed. Then, as shown in FIG. 29, by using an Au paste, a pattern 224b is printed on the fired main electrode layer at the corresponding position, followed by secondary metallization. In the secondary metallization, the printed pattern 224b is fired at a temperature (for example, 850° C. to 1000° C.) lower than a ceramics firing temperature. Thus, the multilayered third electrode 19 is formed, to thereby complete the pumping cell unit 111.

Figure 30:
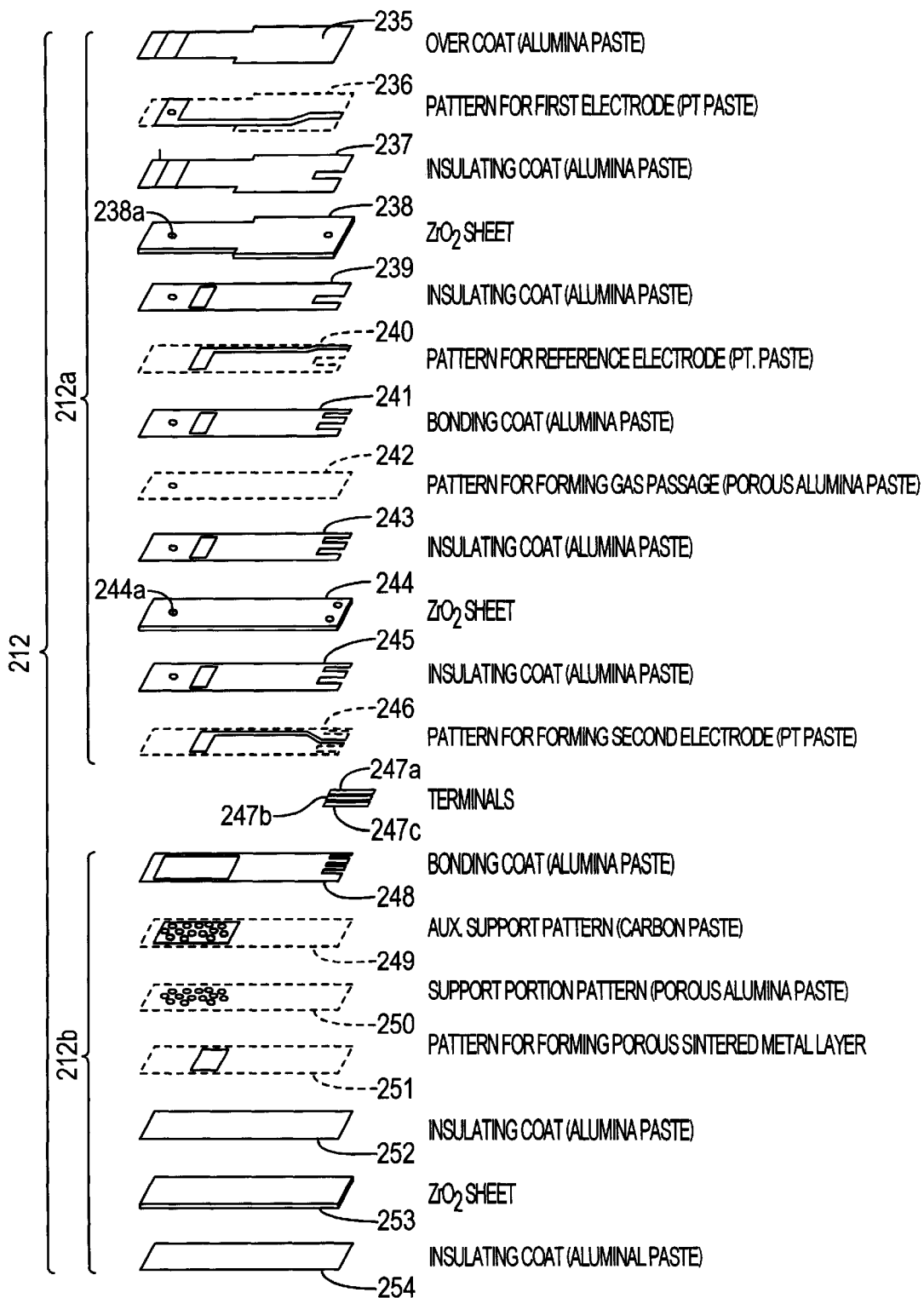
FIG. 30 is an exploded perspective view showing a method of manufacturing the sensor cell unit of the gas sensor of FIG. 26.

FIG. 30 shows a laminate structure of a second unfired assembly 212 used for manufacturing the sensor cell unit 112. The second unfired assembly 212 includes a first portion 212a and a second portion 212b. The first portion 212a is mainly composed of a green sheet 238, which will serve as a main portion of the oxygen concentration cell element 4, and a green sheet 244, which will serve as a main portion of the combustible gas component concentration detection element 5. The second portion 212b is mainly composed of a green sheet 253, which will serve as the shield member 6.

In the first portion 212a, insulating coats 237 and 239 for insulating the leads 15a and 14a from the first cell element 4 are formed on the corresponding surfaces of the green sheet 238 in regions other than those corresponding to the electrodes 15 and 14 (FIG. 26). After the insulating coats 237 and 239 are formed, electrode patterns 236 and 240 for forming the electrodes 15 and 14 and the leads 15a and 14a are formed by printing using a Pt paste or the like. Insulating coats 243 and 245 are formed on the corresponding surfaces of the green sheet 244. An electrode pattern 246 for forming the electrode 16 and the lead 16a is formed on the insulating coat 245. The thus-processed green sheets 238 and 244 are bonded together using a bonding coat 241. Through-holes 238a and 244a for forming the second gas passage 13 are formed in the green sheets 238 and 244. Printing of a pattern 242 causes the through-holes 238a and 244a to be filled with $Al_2O_3$ paste. Cuts, which will serve as fitting depressions 112a (FIG. 27), are formed in the green sheet 238 at widthwise edge portions. A protective over coat 235 is formed on the electrode pattern 236, which will serve as the first electrode 16, using an $Al_2O_3$ paste or the like.

In the second portion 212b, insulating coats 252 and 254 are formed on the corresponding surfaces of the green sheet 253. A pattern 251 for forming a porous sintered metal layer for accelerating combustion of a combustible gas component is formed on the insulating coat 252 by printing using a Pt paste or the like (the pattern 251 may be omitted). A support portion pattern 250 and an auxiliary support pattern 249 are formed above the insulating coat 252 in order to form the second processing space 10 in a manner similar to that shown in FIG. 4.

The first portion 212a and the second portion 212b are bonded together using a bonding coat 248, while end portions of Pt—Rh alloy wires 247a, 247b and 247c, which will serve as terminals of the electrodes 15, 14 and 16, are sandwiched between the portions 212a and 212b. The thus-obtained second unfired assembly 212 is fired to obtain the sensor cell unit 112 shown in FIG. 26.

EXAMPLE 1

In the gas sensor 1 shown in FIG. 1, the elements 3 to 5 and the shield member 6 were formed of $ZrO_2$ solid electrolyte containing $Y_2O_3$ in an amount of 5% by weight. Among the porous electrodes 14 to 16, 19 and 20, the electrodes 15 and 19 were formed of a PtAu alloy containing Au in an amount of 1% by weight, and other electrodes were formed of Pt. The first processing space 9 and the second processing space 10 had a height of 0.02 mm, a width of 22 mm, and a length of 7 mm. The sensor 1 was incorporated into the gas sensor system 50 of FIG. 5. The test gas was composed of oxygen (7%), water vapor (10%), carbon dioxide (10%), nitrogen monoxide (500 ppm), methane as a combustible gas component (0 to 500 ppmC) and nitrogen (balance). The sensor 1 was held in the test gas and heated by the heaters 2 and 8 so as to heat the elements 3 to 5 to a temperature of 650° C.

Figure 10:
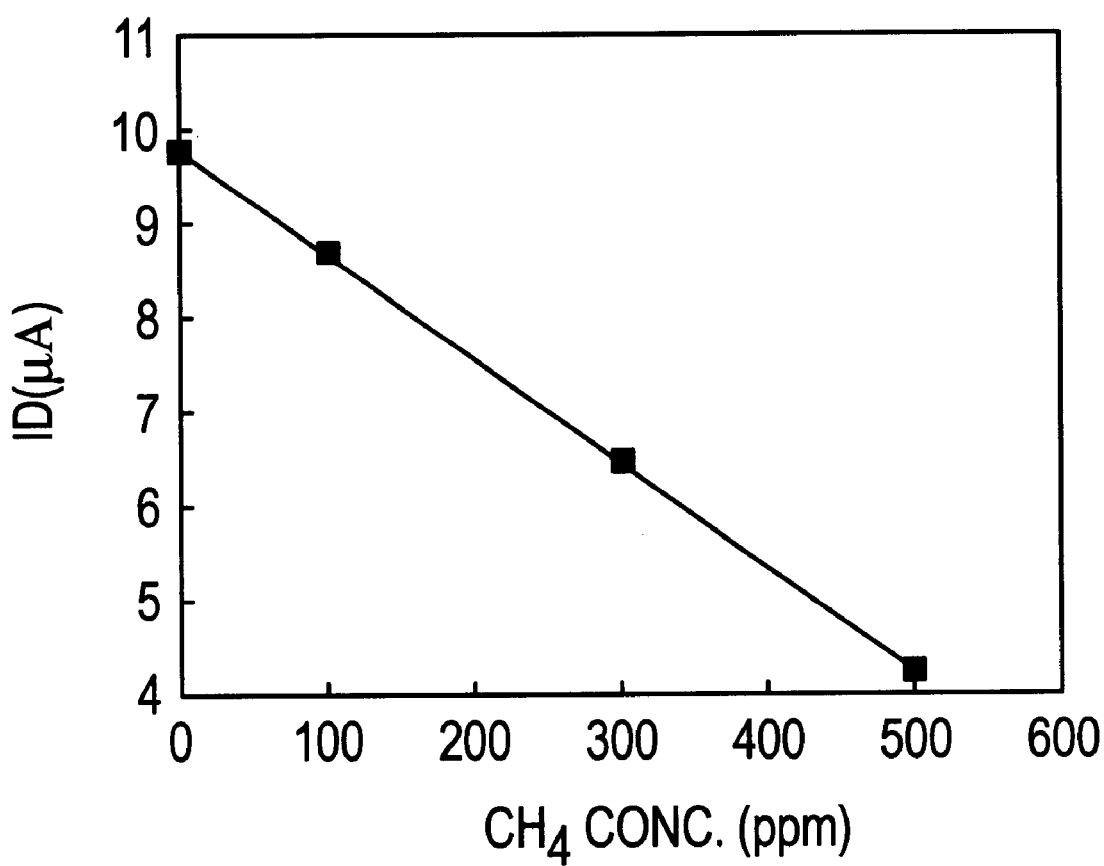
FIG. 10 is a graph showing sensor output as a function of methane concentration obtained in the experiment of Example 1.

The target electromotive force EC of the oxygen concentration cell element 4 was set to a value (approximately 550 mV) such that the target oxygen concentration Px of the first processing space 9 was $10^{-11}$ atm. Under those conditions, the output current Id of the combustible gas component concentration detection element 5 was examined to see how it varied with the methane concentration of the test gas. Notably, the constant-voltage regulated DC power source 58 (FIG. 5) applied a voltage VC of 250 mV to the combustible gas component concentration detection element 5. The results are shown in FIG. 10. As seen from FIG. 10, the output current Id of the gas sensor 1 changed greatly with methane concentration, indicating that the sensor 1 exhibits good sensitivity toward methane.

Figure 11:
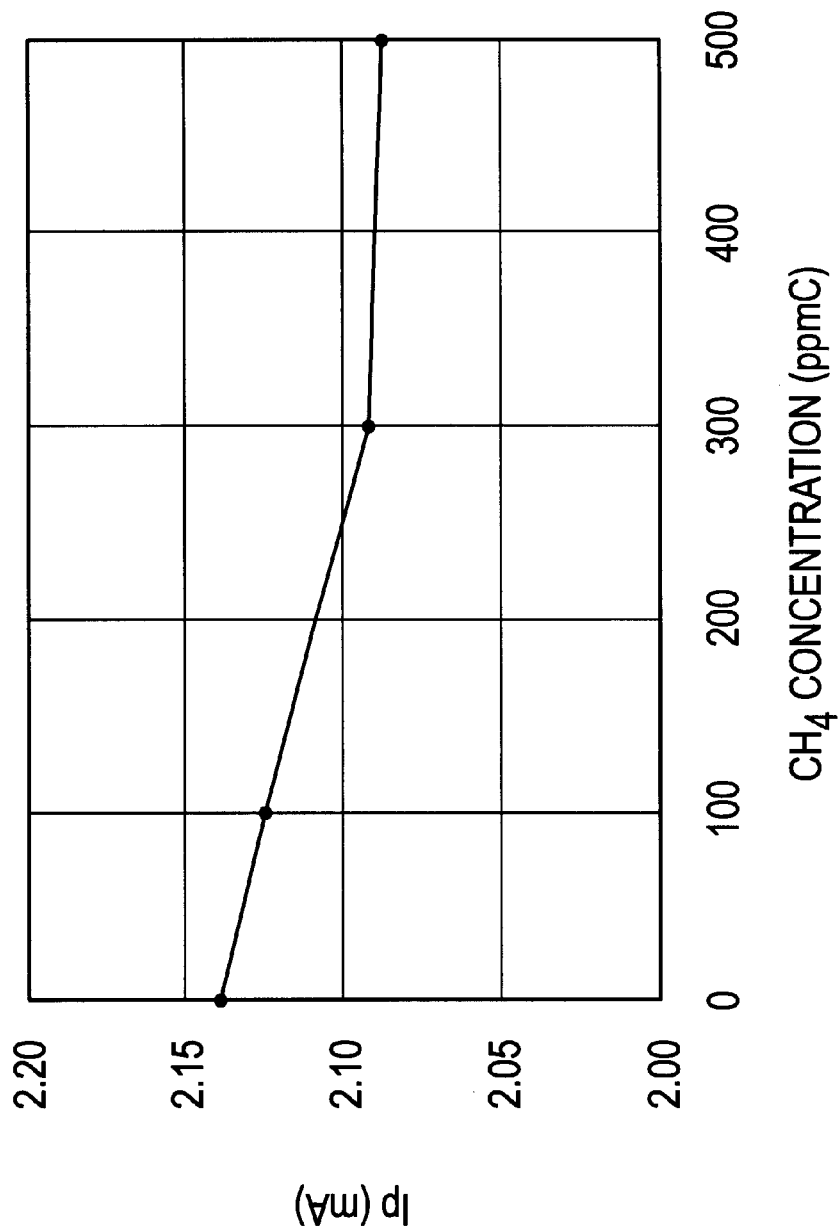
FIG. 11 is a graph showing the methane concentration obtained in the experiment of Example 1.

FIG. 11 shows the relationship between methane concentration and the pumping current Ip of the oxygen pumping element 3. As seen from FIG. 11, the pumping current Ip decreased as the methane concentration increased. This indicates that at the above setting of the oxygen concentration of the first processing space 9, a portion of the methane component is burned. Specifically, as the methane concentration increases, the amount of burned methane increases. Thus, it is considered that the amount of oxygen pumped out by the oxygen pumping element 3 decreases in order to maintain the target oxygen concentration, i.e., the pumping current Ip.

EXAMPLE 2

Figure 12:
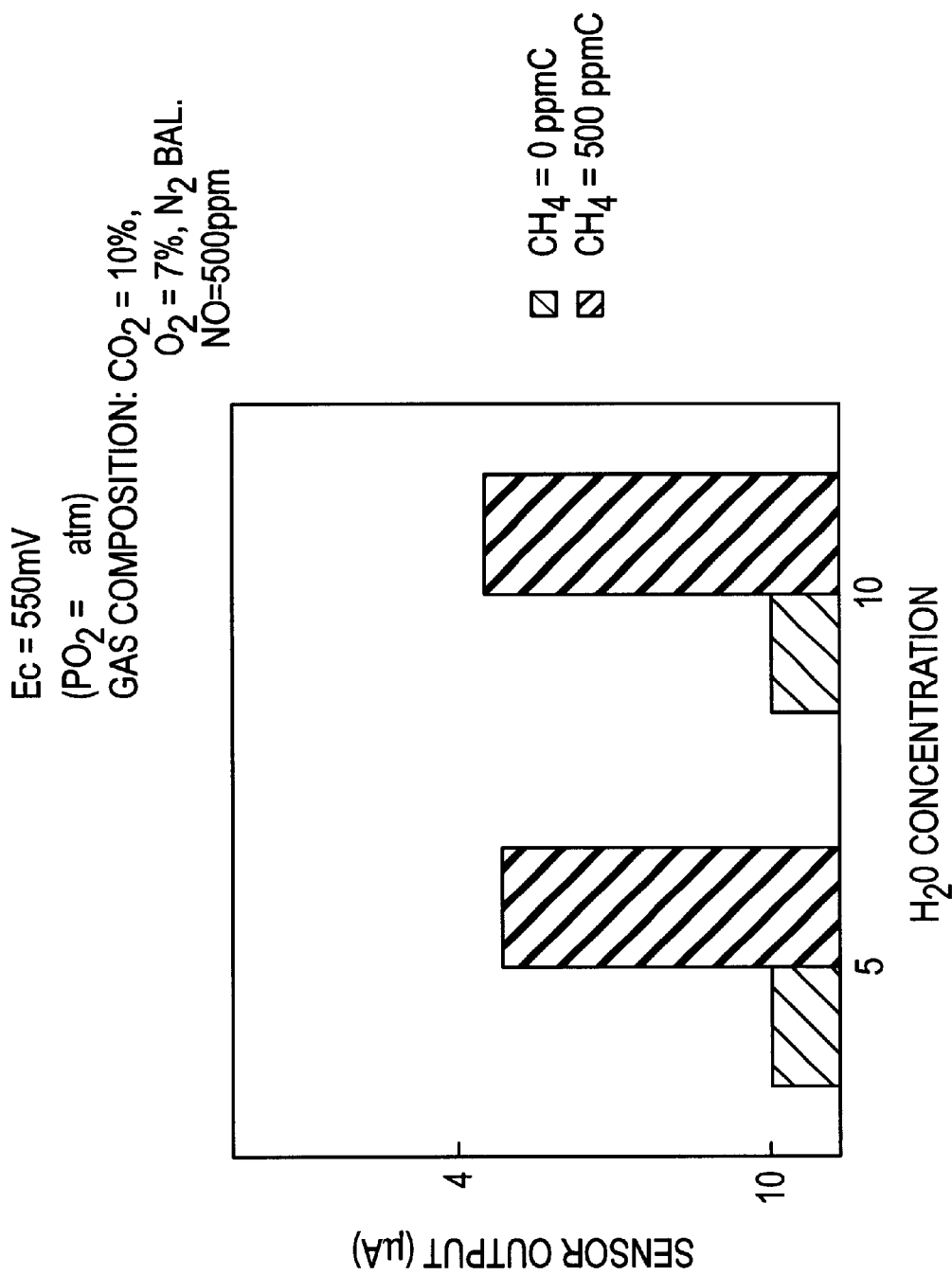
FIG. 12 is a graph showing the influence of water vapor concentration on the sensor output obtained in the experiment of Example 2.
Figure 13:
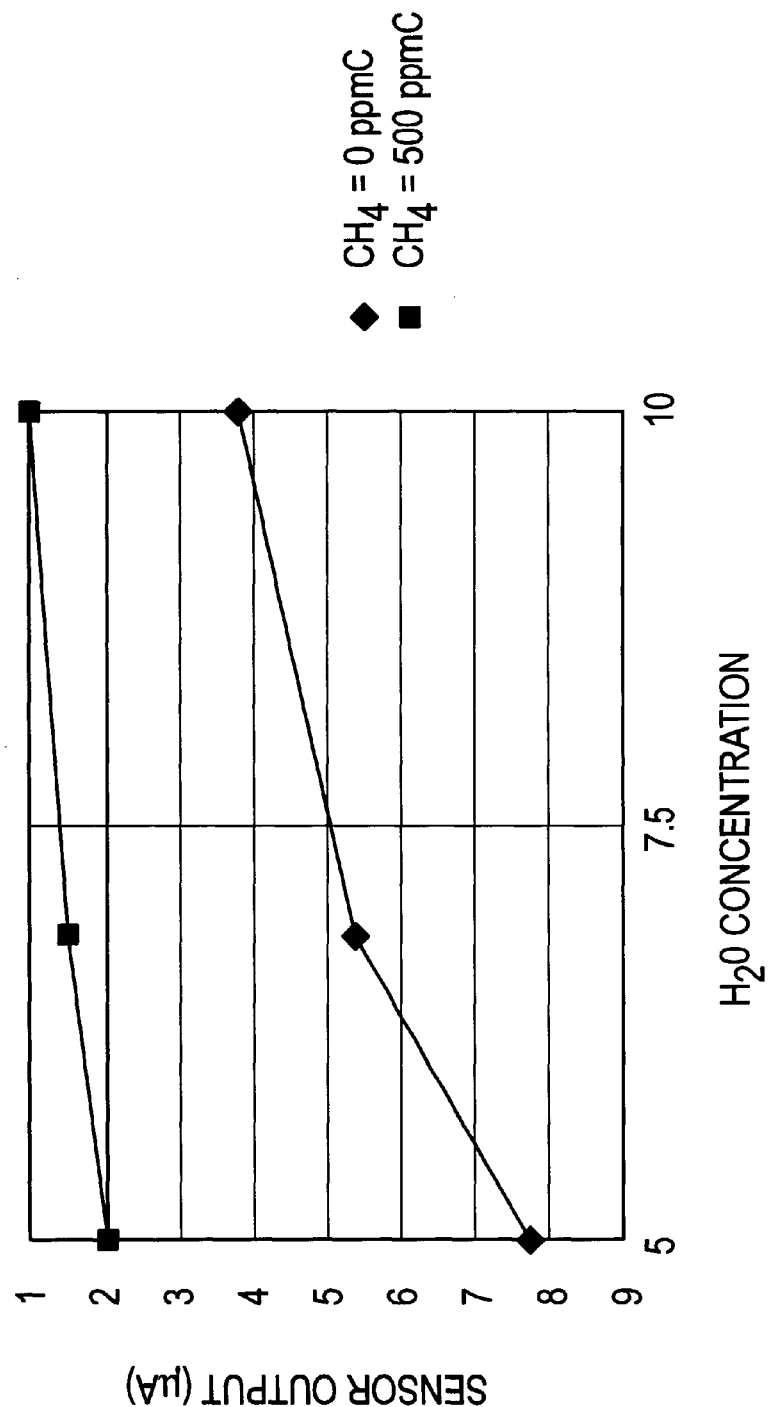
FIG. 13 is a graph showing the effect of water vapor concentration on the sensor output obtained in an experiment of the Comparative Example for comparison with Example 2.

An experiment similar to that of Example 1 was conducted using the sensor system 50 of Example 1. The concentrations of test gas components were similar to those used in Example 1, except that the methane concentration was either 0 ppmC or 500 ppmC and the water vapor concentration was either 5% or 10%. The results are shown in FIG. 12. Specifically, the output current Id corresponding to either methane concentration remained almost unchanged for a water vapor concentration of 5% and 10%. This indicates that in the gas sensor 1, decomposition of water vapor is hardly initiated during measurement, and thus the methane concentration can be stably measured regardless of the water vapor concentration. As a Comparative Example, the target electromotive force EC of the oxygen concentration cell element 4 was set to a value (approximately 651 mV) such D that the target oxygen concentration Px of the first processing space 9 was $10^{-13}$ atm. An experiment was conducted in a manner similar to that of the present Example 2. The results are shown in FIG. 13. As seen from FIG. 13, the sensor output was significantly influenced by the water vapor concentration.

[0109]

EXAMPLE 3

An experiment was conducted using the sensor system 50 of Example 1. The test gas was composed of methane (500 ppmC), nitrogen monoxide (500 ppm), oxygen (7%), water vapor (3% to 15%), carbon dioxide (10%) and nitrogen (balance). The gas sensor 1 was held in the test gas and heated by means of the heaters 2 and 8 so as to heat the elements 3 to 5 to a temperature of 650 C. The target electromotive force EC of the oxygen concentration cell element 4 was set to various values (250 mV (corresponding to $10^{-5}$ atm) to 750 mV (corresponding to $10^{-15}$ atm)) such that the target oxygen concentration Px of the first processing space 9 was $10^{-15}$ atm to $10^{-5}$ atm. Under these conditions, the output current Id of the combustible gas component concentration detection element 5 was measured. Notably, the constant-voltage regulated DC power source 58 (FIG. 5) applied a voltage VC of 250 mV to the combustible gas component concentration detection element 5.

Figure 14:
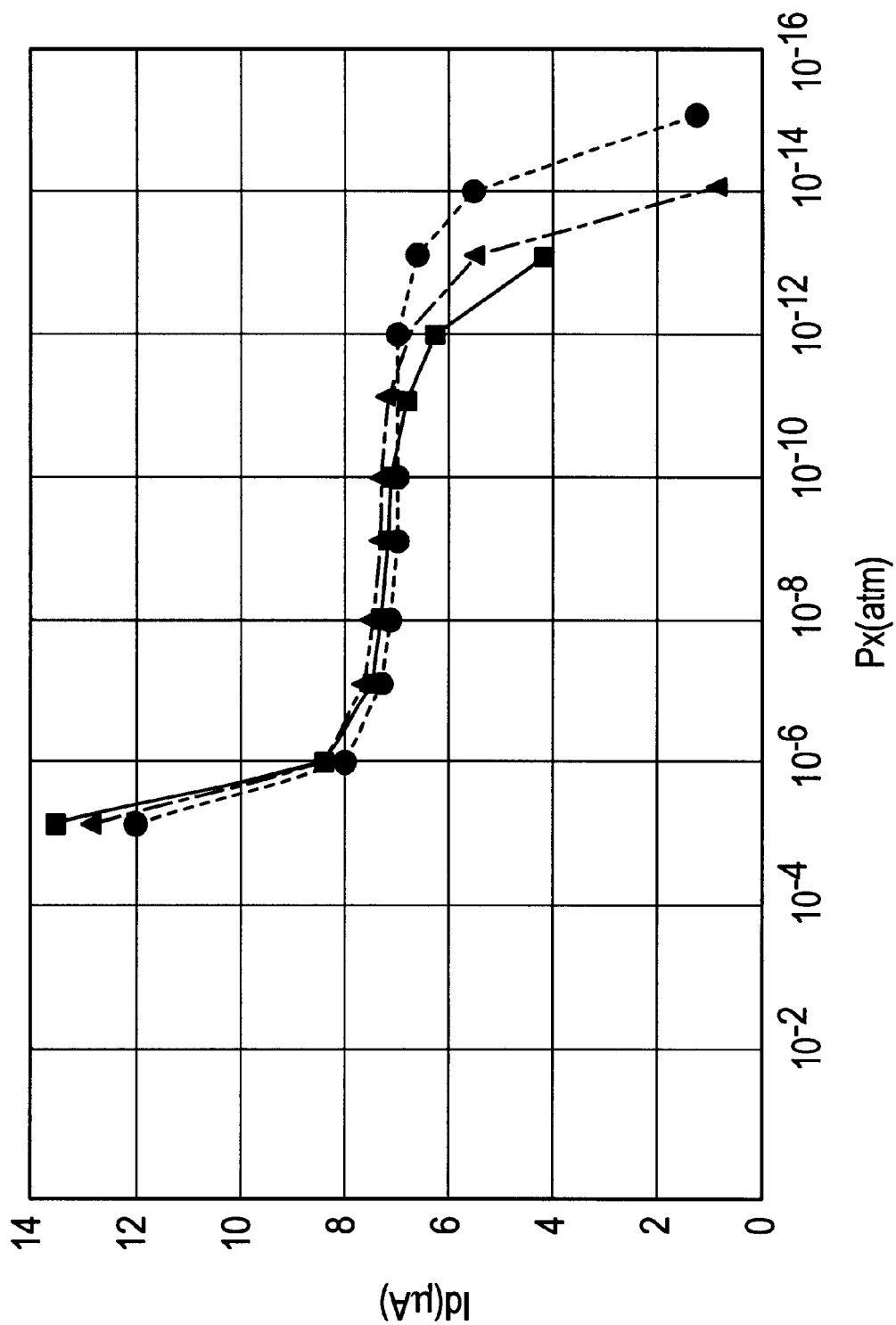
FIG. 14 is a graph showing the effect of oxygen concentration in the first processing space on sensor sensitivity obtained in the experiment of Example 3.

FIG. 14 shows the relationship between Id and Px with water vapor concentrations taken as parameters (circle: 3% water vapor; triangle: 10% water vapor; square: 15% water vapor). As seen from FIG. 14, at a Px value of $10^{-12}$ atm to $10^{-6}$ atm, a substantially constant sensor output is obtained irrespective of the Px value for any of the water vapor concentrations. At a PX value of $10^{-12}$ atm or lower, Id, which is expected to be constant, exhibited a sharp decrease (i.e., an increase in apparent combustible gas component concentration). It is considered that this is because a large amount of hydrogen, which is a combustible gas component, was generated as a result of water vapor decomposition. At a Px value of $10^{-6}$ atm or higher, Id exhibited a sharp increase (i.e., a decrease in apparent combustible gas component concentration). It is considered that this is because methane was burned within the first processing space, i.e., the methane concentration was reduced due to excess oxygen.

EXAMPLE 4

Figure 15A:
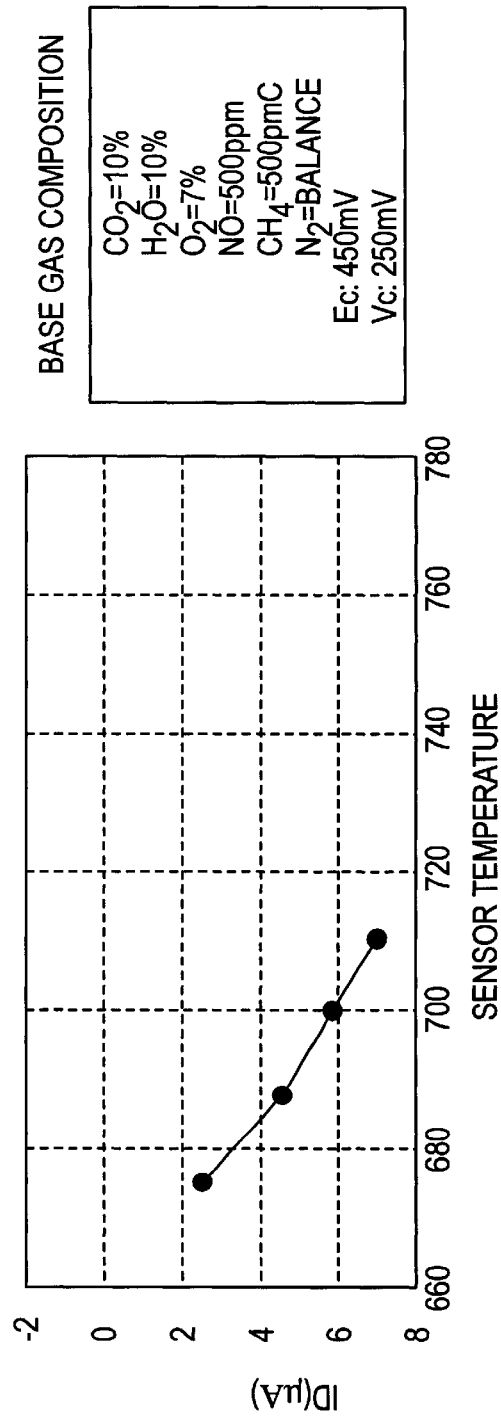
FIGS. 15(*a*) and 15(*b*) are graphs showing the effects of element temperature on sensor output and the oxygen pumping voltage obtained in the experiment of Example 4.
Figure 15B:
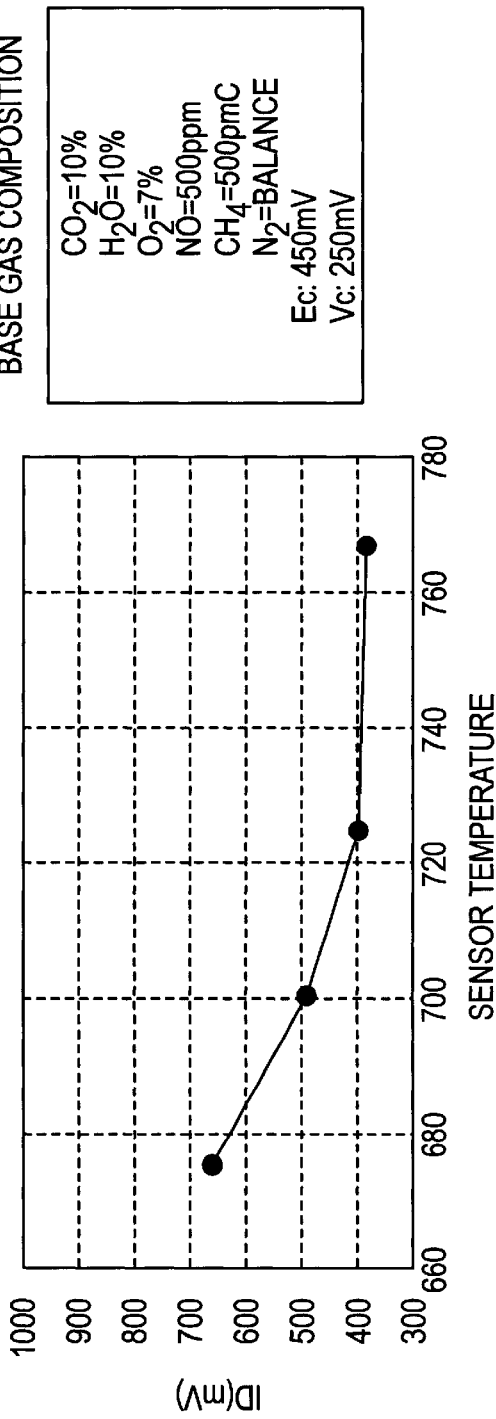

An experiment was conducted using the sensor system 50 of Example 1. The test gas was composed of nitrogen monoxide (500 ppm), methane (500 ppmC) and nitrogen (balance). The gas sensor 1 was held in the test gas and heated by means of the heaters 2 and 8 so as to heat the elements 3 to 5 to a temperature of 600° C. to 770° C. The target electromotive force EC of the oxygen concentration cell element 4 was set to a value (approximately 450 mV) such that the target oxygen concentration Px of the first processing space 9 was $10^{-9}$ atm. Under these conditions, the output current Id of the combustible gas component concentration detection element 5 and the corresponding voltage (pump voltage) VP applied to the oxygen pumping element 3 were measured. Notably, the constant-voltage regulated DC power source 58 (FIG. 5) applied a voltage VC of 250 mV to the combustible gas component concentration detection element 5. The results are shown in FIG. 15. As seen from FIG. 15, at an element temperature in excess of 700° C., the output current Id became excessively low; consequently, the sensitivity of the gas sensor 1 was impaired. Also, as the working temperature decreased, the pumping voltage VP increased. This is because the internal resistance of the oxygen pumping element 3 increases. At an element temperature lower than 650° C., the pumping voltage VP was excessively large; consequently, operation of the oxygen pumping element 3 became unstable.

EXAMPLE 5

Figure 16:
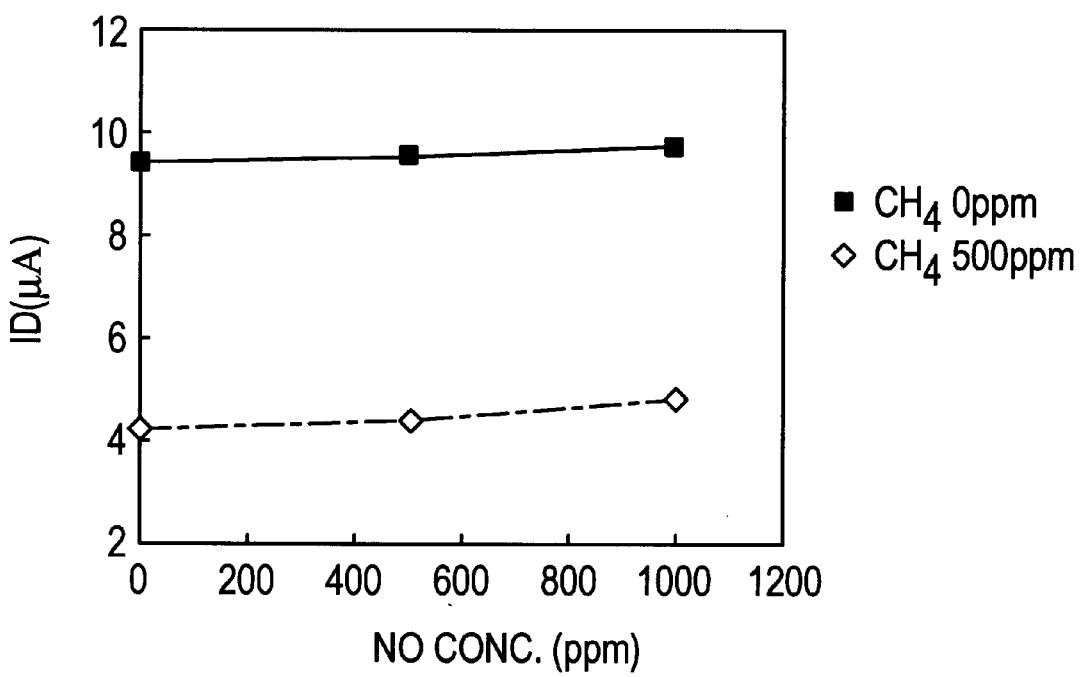
FIG. 16 is a graph showing the effect of nitrogen monoxide concentration of a test gas on the sensor output obtained in the experiment of Example 5.

An experiment was conducted using the sensor system 50 of Example 1. The test gas was composed of methane (0 ppmC or 500 ppmC), oxygen (7%), water vapor (10%), carbon dioxide (10%), nitrogen monoxide (0, 500, or 1000 ppm) and nitrogen (balance). The gas sensor 1 was held in the test gas and heated by means of the heaters 2 and 8 so as to heat the elements 3 to 5 to a temperature of 650° C. The target electromotive force EC of the oxygen concentration cell element 4 was set to a value (approximately 450 mV) such that the target oxygen concentration Px of the first processing space 9 was $10^{-9}$. Under these conditions, the output current Id of the combustible gas component concentration detection element 5 was measured. Notably, the constant-voltage regulated DC power source 58 (FIG. 5) applied a voltage VC of 250 mV to the combustible gas component concentration detection element 5. The results are shown in FIG. 16. As seen from FIG. 16, the output current Id was hardly influenced by the NO concentration.

EXAMPLE 6

Figure 17:
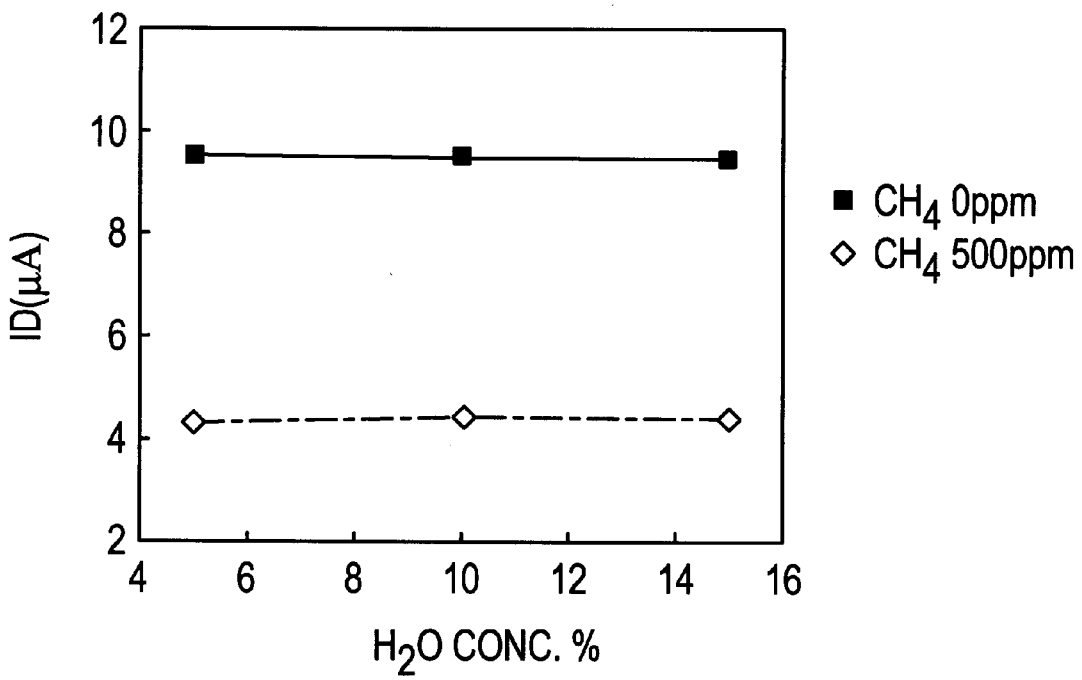
FIG. 17 is a graph showing the effect of water vapor concentration of a test gas on the sensor output obtained in the experiment of Example 6.

An experiment was conducted using the sensor system 50 of Example 1. The test gas was composed of methane (0 ppmC or 500 ppmC), oxygen (7%), nitrogen monoxide (500 ppm), carbon dioxide (10%), water vapor (5%, 10%, or 15%) and nitrogen (balance). The gas sensor 1 was held in the test gas and heated by means of the heaters 2 and 8 so as to heat the elements 3 to 5 to a temperature of 650° C. The target electromotive force EC of the oxygen concentration cell element 4 was set to a value (approximately 450 mV) such that the target oxygen concentration Px of the first processing space 9 was $10^{-9}$. Under these conditions, the output current Id of the combustible gas component concentration detection element 5 was measured. Notably, the constant-voltage regulated DC power source 58 (FIG. 5) applied a voltage VC of 250 mV to the combustible gas component concentration detection element 5. The results shown in FIG. 17. As seen from FIG. 17, the output current Id was hardly influenced by the water vapor concentration.

EXAMPLE 7

Figure 18:
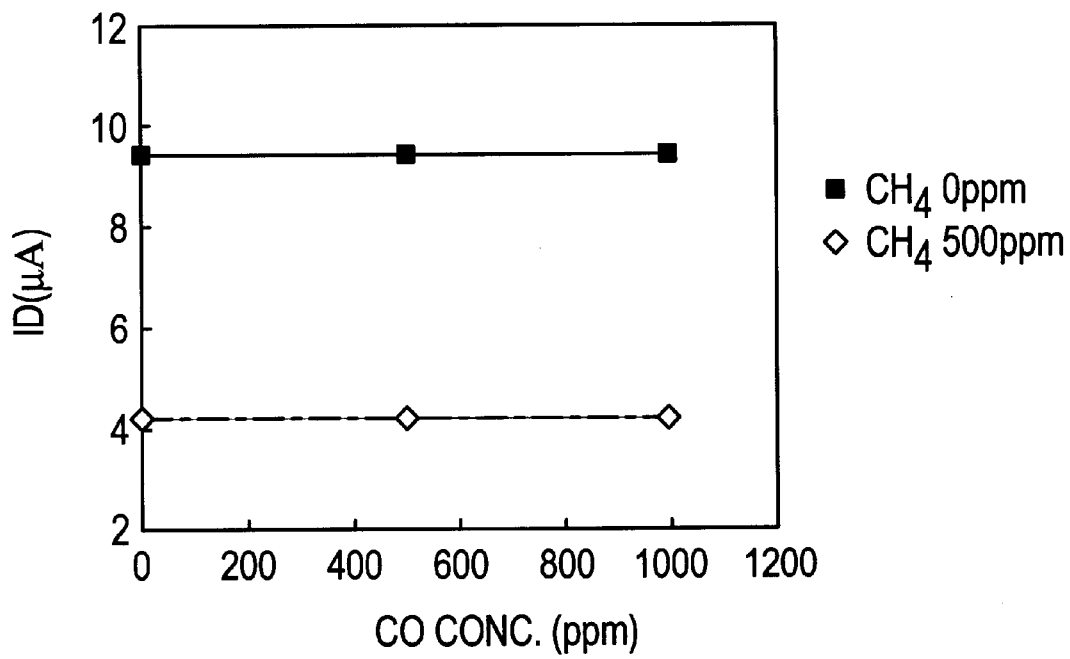
FIG. 18 is a graph showing the effect of carbon monoxide concentration of a test gas on the sensor output obtained in the experiment of Example 7.

An experiment was conducted using the sensor system 50 of Example 1. The test gas was composed of methane (0 ppmC or 500 ppmC), oxygen (7%), water vapor (10%), nitrogen monoxide (500 ppm), carbon dioxide (10%), carbon monoxide (0, 500, or 1000 ppm) and nitrogen (balance). The gas sensor 1 was held in the test gas and heated by means of the heaters 2 and 8 so as to heat the elements 3 to 5 to a temperature of 650° C. The target electromotive force EC of the oxygen concentration cell element 4 was set to a value (approximately 450 mV) such that the target oxygen concentration Px of the first processing space 9 was $10^{-9}$. Under these conditions, the output current Id of the combustible gas component concentration detection element 5 was measured. Notably, the constant-voltage regulated DC power source 58 (FIG. 5) applied a voltage VC of 250 mV to the combustible gas component concentration detection element 5. The results are shown in FIG. 18. As seen from FIG. 18, the output current Id was hardly influenced by the carbon monoxide concentration.

EXAMPLE 8

Figure 19:
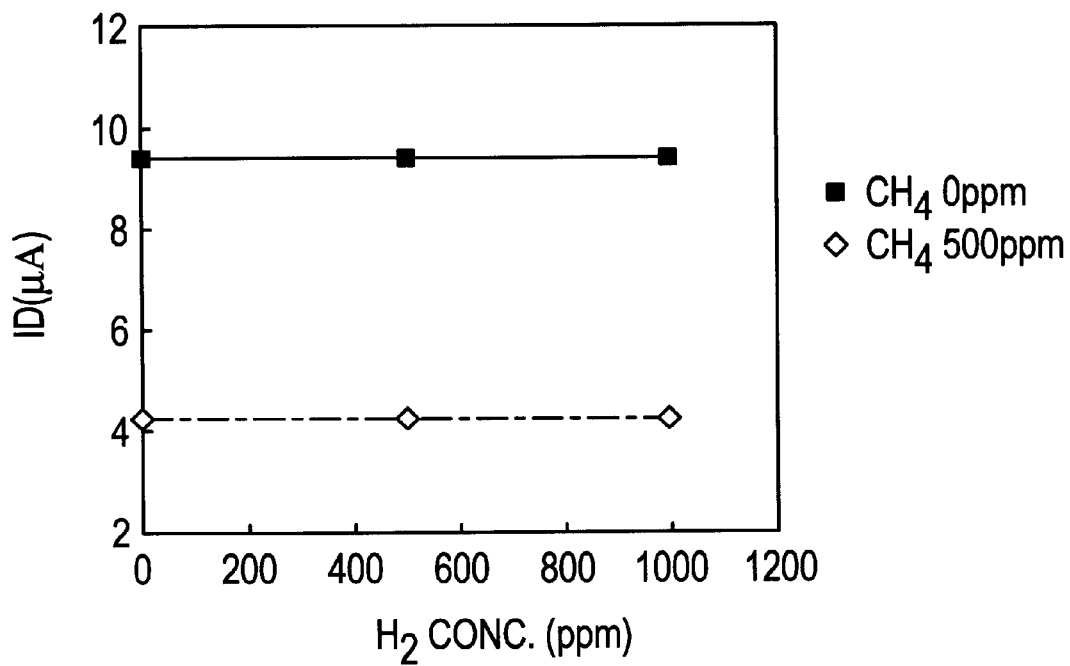
FIG. 19 is a graph showing the effect of hydrogen concentration of a test gas on the sensor output obtained in the experiment of Example 8.

An experiment was conducted using the sensor system 50 of Example 1. The test gas was composed of methane (0 ppmC or 500 ppmC), oxygen (7%), water vapor (10%), nitrogen monoxide (500 ppm), carbon dioxide (10%), hydrogen (0, 500, or 1000 ppm) and nitrogen (balance). The gas sensor 1 was held in the test gas and heated by means of the heaters 2 and 8 so as to heat the elements 3 to 5 to a temperature of 650° C. The target electromotive force EC of the oxygen concentration cell element 4 was set to a value (approximately 450 mV) such that the target oxygen concentration Px of the first processing space 9 was $10^{-9}$. Under these conditions, the sensor and the output current Id of the combustible gas component concentration detection element 5 was measured. Notably, the constant-voltage regulated DC power source 58 (FIG. 5) applied a voltage VC of 250 mV to the combustible gas component concentration detection element 5. The results are shown in FIG. 19. As seen from FIG. 19, the output current Id was hardly influenced by the hydrogen concentration. This is considered to be the case because hydrogen contained in the exhaust gas is mostly consumed by combustion when the exhaust gas is introduced into the first processing space.

EXAMPLE 9

Figure 20:
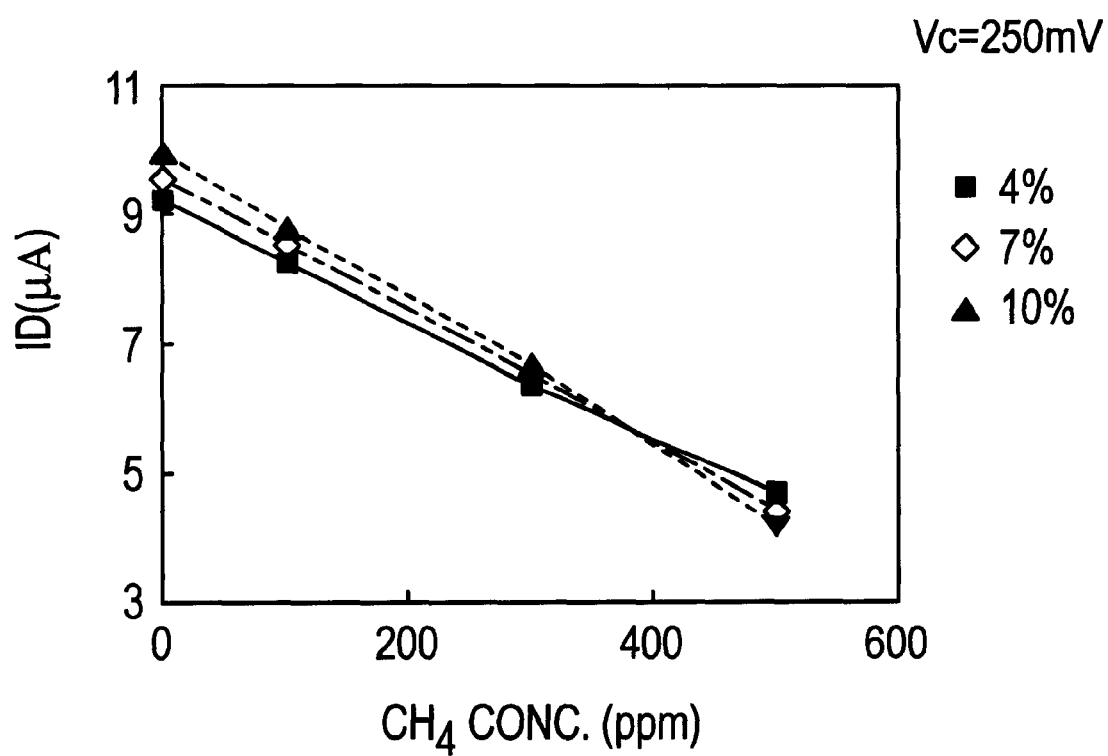
FIG. 20 is a graph showing the effect of oxygen concentration of a test gas on the sensor output obtained in the experiment of Example 9.

An experiment was conducted using the sensor system 50 of Example 1. The test gas was composed of oxygen (4%, 7%, or 10%), water vapor (10%), nitrogen monoxide (500 ppm), carbon dioxide (10%), methane (0 ppmC to 500 ppmC) and nitrogen (balance). The gas sensor 1 was held in the test gas and heated by means of the heaters 2 and 8 so as to heat the elements 3 to 5 to a temperature of 650° C. The target electromotive force EC of the oxygen concentration cell element 4 was set to a value (approximately 450 mV) such that the target oxygen concentration Px of the first processing space 9 was $10^{-9}$. Under these conditions, the output current Id of the combustible gas component concentration detection element 5 was measured. Notably, the constant-voltage regulated DC power source 58 (FIG. 5) applied a voltage VC of 250 mV to the combustible gas component concentration detection element 5. The results are shown in FIG. 20. As seen from FIG. 20, the methane concentration dependency of the output current Id was hardly influenced by the oxygen concentration.

EXAMPLE 10

Figure 21A:
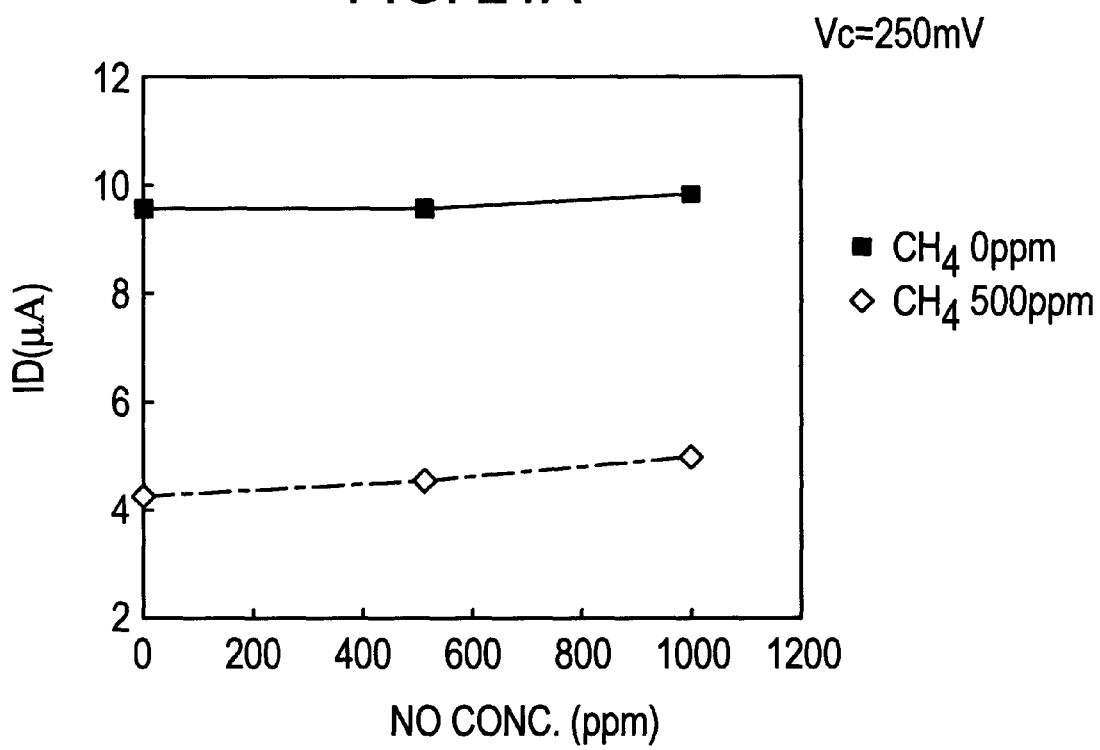
FIGS. 21(*a*) and 21(*b*) are graphs showing the effect of nitrogen monoxide concentration of a test gas on the sensor output, and the relationship between that effect and the voltage applied to the combustible gas component concentration detection element obtained in the experiment of Example 10.
Figure 21B:
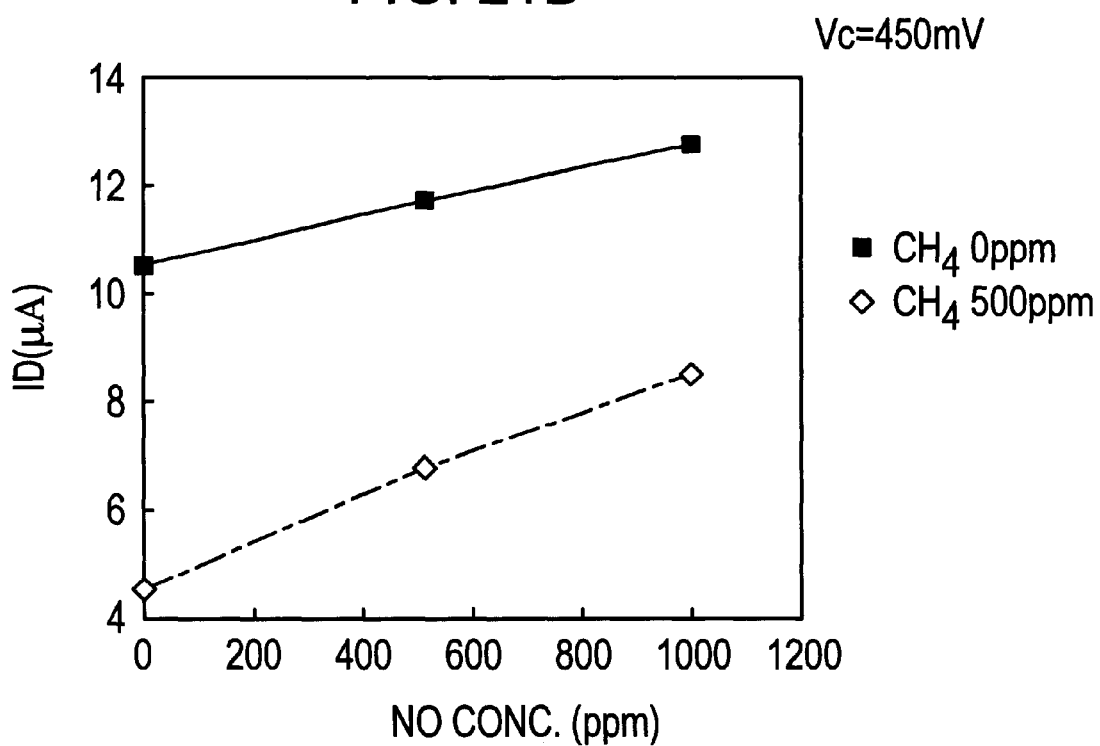

An experiment was conducted using the sensor system 50 of Example 1. The test gas was composed of methane (0 ppmC to 500 ppmC), oxygen (7%), water vapor (10%) nitrogen monoxide (0, 500, or 1000 ppm), carbon dioxide (10%) and nitrogen (balance). The gas sensor 1 was held in the test gas and heated by means of the heaters 2 and 8 so as to heat the elements 3 to 5 to a temperature of 650° C. The target electromotive force EC of the oxygen concentration cell element 4 was set to a value (approximately 450 mV) such that the target oxygen concentration Px of the first processing space 9 was $10^{-9}$. The constant-voltage regulated DC power source 58 (FIG. 5) applied a voltage VC of 250 mV or 450 mV to the combustible gas component concentration detection element 5. Under these conditions, the output current Id of the combustible gas component concentration detection element 5 was measured. The results are shown in FIG. 21. As seen from FIG. 21, the output current Id was hardly influenced by the nitrogen monoxide concentration at a VC value of 250 mV.

EXAMPLE 11

In the gas sensor 100 shown in FIG. 26, the porous electrodes 14 to 16 and 20 were formed using a Pt—Au (1% by weight) alloy. The third electrode 19 was a two-layered electrode composed of the main electrode layer 151 (FIG. 28) and the surface electrode layer 152. The main electrode layer 151 was integrally formed with the pumping cell unit 111 using a Pt—Au (1% by weight) alloy and by firing. An Au paste was applied to the main electrode layer 151, followed by secondary firing (at 900° C.) to thereby form the surface electrode layer 152. As in the case of Example 1, the first processing space 9 and the second processing space 10 each had a height of 0.02 mm, a width of 22 mm and a length of 7 mm. A section was taken across the thickness of the third electrode 19. The composition of the section was analyzed using an Electron Probe Micro Analyzer (EPMA; energy diffusion system). As a result, the Au content was found to be about 4.1% by weight when a total content of Au and Pt in the main electrode portion was taken as 100% by weight. It was confirmed that the surface electrode layer 152 mainly composed of Au was formed in a surface layer region of the main electrode portion.

The sensor 100 was incorporated into the gas sensor system 50 of FIG. 5. The sensor 100 was held in a test gas composed of oxygen (7%), water vapor (10%), carbon dioxide (10%), nitrogen monoxide (500 ppm), methane (200 ppmC) serving as a combustible gas component and nitrogen (balance). The sensor 100 was heated by means of the heaters 2 and 8 (FIG. 1) so as to heat the elements 3 to 5 to a temperature of 750° C. In the gas sensor 100, the target electromotive force EC of the oxygen concentration cell element 4 was set to a value (about 550 mV) such that the target oxygen concentration Px of the first processing space 9 was $10^{-11}$ atm. Under these conditions, the sensor system 50 was operated to examine how the output current Id of the combustible gas component concentration detection element 5 varies with the methane concentration. Notably, the constant-voltage regulated DC power source 58 (FIG. 5) applied a voltage VC of 350 mV to the combustible gas component concentration detection element 5. The test revealed that in the gas sensor 100, the output current Id corresponding to a methane concentration of 200 ppmC was about 4 μA, which is about twice that observed with the sensor 1 of Example 1. A conceivable reason for such an improvement in sensor sensitivity is that the above-described two-layered structure of the third electrode 19 facilitates combustion of methane to thereby reduce losses associated with combustion of methane within the first processing space 9.

Figure 31A:
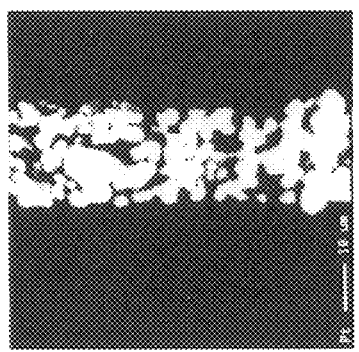
FIGS. 31(*a*), 31(*b*) and 31(*c*) are characteristic X-ray images of a section of the third electrode of a sensor used in Example 11, corresponding to Pt, Au and Zr obtained by EPMA (before aging).
Figure 31B:
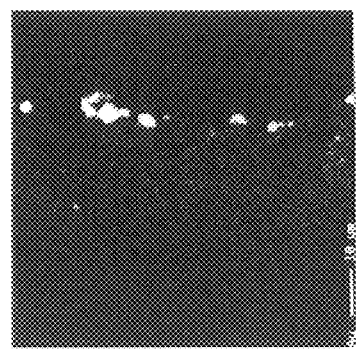
Figure 31C:
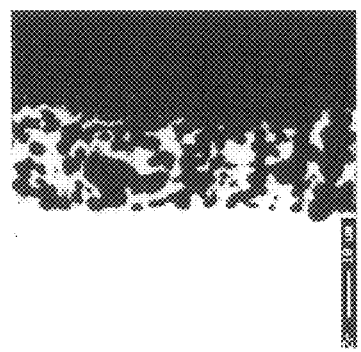

A section of the third electrode which was not used after secondary firing was examined using EPMA attached to an SEM. FIG. 31 shows characteristic X-ray images (about 1000 magnifications) of the section corresponding to Pt (FIG. 31(a)), Au (FIG. 31(b)) and Zr (FIG. 31(c)). In the images shown in FIG. 31, a brighter portion indicates a higher characteristic X-ray intensity (i.e., element concentration). As seen from a comparison of images between FIG. 31(a) and FIG. 31(c), a porous main electrode layer of Pt was formed as thick as about 20 μm on a solid electrolyte layer mainly composed of $ZrO_2$. In order to improve the bonding strength of the electrode by reducing the difference in thermal expansion coefficient between the porous electrode and the solid electrolyte layer, Pt paste blended with $ZrO_2$ powder was used as an electrode material. Thus, a region of distribution associated with characteristic X-ray of Zr was observed in the main electrode layer. As seen from a comparison of images between FIG. 31(a) and FIG. 31(b), a surface electrode layer mainly composed of Au was formed in an outermost surface layer portion of the main electrode layer. Notably, a thin dispersion of the characteristic X-ray of Au was observed in a region corresponding to the main electrode layer. It is considered that in this case, Au diffused from the surface electrode layer side to the main electrode layer side during secondary firing.

Figure 32A:
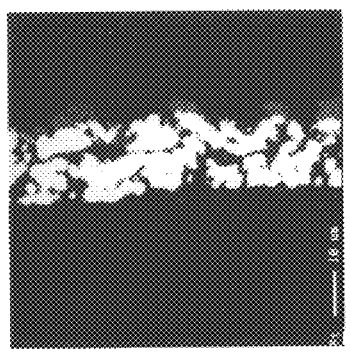
FIGS. 32(*a*), 32(*b*) and 32(*c*) are characteristic X-ray images of a section of the third electrode of a sensor used in Example 11, corresponding to Pt, Au and Zr obtained by EPMA (after aging).
Figure 32B:
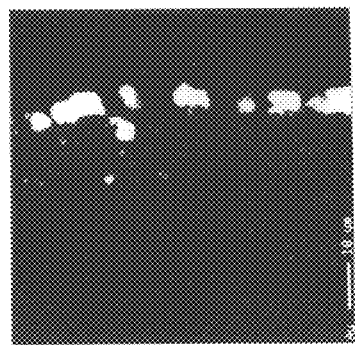
Figure 32C:
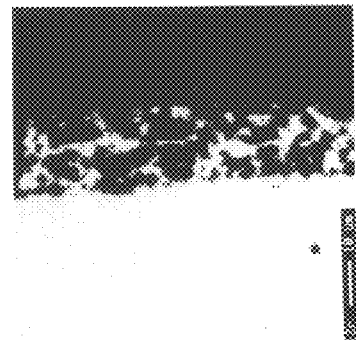

Next, the sensor was aged for 500 hours at 780° C. in the atmosphere. Subsequently, the section of the third electrode was examined by EPMA. FIG. 32 shows characteristic X-ray images (about 1000 magnifications) of the section corresponding to Pt (FIG. 32(a)), Au (FIG. 32(b)) and Zr (FIG. 32(c)). As compared to FIG. 31, the surface electrode layer region having a high Au concentration was wider, and the Pt concentration of the region was higher. Acceding to an Au—Pt equilibrium phase diagram, at 780° C., the solid-solution limit of Pt on the Au side was as high as about 20% by weight, while the solid-solution limit of Au on the Pt side was as low as about 5% by weight. In the main electrode layer, secondary firing most likely caused an increase in the Au concentration in the vicinity of the interface with the surface electrode layer to near a saturation concentration in Pt. Accordingly, the above-described aging is considered to cause the following tendencies: diffusion of Au from the surface electrode layer side to the main electrode layer side is relatively difficult, while diffusion of Pt from the main electrode layer side to the surface electrode layer side progresses relatively easily.

As a result, diffusion of Pt to the surface electrode layer side is considered to have advanced having priority over diffusion of Au to the main electrode layer side, resulting in expansion of the surface electrode layer region. As a result of this aging, the Pt concentration of the surface electrode layer increased to about a solid-solution limit of Pt in Au (for example, 20% by weight at 780° C.). However, a Pt concentration up to this level still allows for the effect of suppressing the combustion-related catalytic activity by means of the surface electrode layer. Also, a small time-course variation in Pt concentration of the surface electrode layer while the sensor is being used may advantageously improve the time-course stability of the sensor characteristics (for example, the offset electromotive force of the oxygen concentration cell element). In this case, it is desirable to positively age the sensor in the above manner before shipment so as to sufficiently diffuse Pt to the surface electrode layer side.

While the invention has been described in detail and with reference to specific embodiments thereof, it will be apparent to one skilled in the art that various changes and modifications can be made therein without departing from the spirit and scope thereof.

What is claimed is:

1. A gas sensor comprising:

a first processing space and a first gas passage for introducing a measuring gas containing oxygen, water vapor and a combustible gas component into said first processing space;

a second processing space and a second gas passage for introducing a gas contained in said first processing space into said second processing space;

an oxygen concentration detection element for measuring the oxygen concentration of gas contained in said first processing space;

an oxygen pumping element comprising an oxygen-ion conductive solid electrolyte having electrodes formed on opposing surfaces thereof, said oxygen pumping element pumping out oxygen from said first processing space or pumping oxygen into said first processing space such that the oxygen concentration of the measurement gas introduced into said first processing space and measured by said oxygen concentration detection element falls within a range of $10^{-12}$ atm to $10^{-6}$ atm;

an oxidation catalyst for accelerating combustion of a combustible gas component contained in the gas which has been introduced into said second processing space from said first processing space via the second gas passage;

a combustible gas component concentration detection element for providing information regarding the concentration of the combustible gas component of the measurement gas, comprising an oxygen-ion conductive solid electrolyte having electrodes formed on opposing surfaces thereof, one of said electrodes is exposed to said second processing space and is arranged so as not to contact said second gas passage, said combustible gas component concentration detection element having an output current which varies according to the amount of oxygen consumed by combustion of the combustible gas component when a constant voltage is applied to the electrodes of the combustible gas component concentration detection element, to thereby provide information regarding the concentration of the combustible gas component of the measurement gas.

2. The gas sensor according to claim 1, wherein the constant voltage is applied to the electrodes of said combustible gas component concentration detection element in a polarity such that the electrode exposed to said second processing space becomes negative.

3. The gas sensor according to claim 1, wherein said oxygen pumping element adjusts the oxygen concentration of the measurement gas introduced into said first processing space and measured by said oxygen concentration detection element within a range such that water vapor contained in the measurement gas is not substantially decomposed.

4. The gas sensor according to claim 1, wherein said combustible gas component comprises hydrocarbon and another combustible gas component, said oxygen pumping element adjusts the oxygen concentration within said first processing space as measured by said oxygen concentration detection element within a range such that a combustible component of the measurement gas having a higher combustion activity than hydrocarbon is burned more readily than hydrocarbon.

5. The gas sensor according to claim 1, wherein said oxygen concentration detection element comprises an oxygen concentration cell element comprising an oxygen-ion conductive solid electrolyte having electrodes formed on opposing surfaces thereof, one of the electrodes of the oxygen concentration cell elements is exposed to said first processing space and is defined as a first electrode;

the electrode of said combustible gas component concentration detection element exposed to said second processing space is defined as a second electrode; and said first and second electrodes comprising a porous electrode having oxygen molecule desorbent capability, said second electrode serving as an oxidation catalyst having oxidation-catalytic activity toward a combustible gas component contained in the measurement gas, and said first electrode having a lower oxidation-catalytic activity than said second electrode.

6. The gas sensor according to claim 5, comprising a partition wall formed of an oxygen-ion conductive solid electrolyte disposed between said first and second processing spaces;

the second gas passage is formed in the partition wall so as to establish communication between said first processing space and said second processing space, said gas sensor further comprising an oxygen reference electrode embedded in the partition wall at a thicknesswise intermediate portion thereof;

the first electrode is formed on the partition wall so as to be exposed to said first processing space, wherein the first electrode, the oxygen reference electrode and a portion of the partition wall interposed between the first electrode and the oxygen reference electrode constitute said oxygen concentration cell element; and the second electrode is formed on the partition wall so as to be exposed to said second processing space, wherein the second electrode, the oxygen reference electrode, and a portion of the partition wall interposed between the second electrode and the oxygen reference electrode constitute said combustible gas component concentration detection element.

7. The gas sensor according to claim 6, wherein at least either the oxygen reference electrode or the second electrode is formed in or on the partition wall at a position so as not to contact said second gas passage.

8. The gas sensor according to claim 5, wherein said oxygen pumping element comprises an oxygen-ion conductive solid electrolyte having electrodes formed on opposing surfaces thereof, one of the electrodes of the oxygen pumping element is exposed to said first processing space and is defined as a third electrode;

the third electrode comprises:
a porous main electrode layer comprising a Pt—Au alloy or Pt; and
a porous surface electrode layer covering the main electrode layer, said surface electrode layer comprising a material selected from the group consisting of a metal containing Au or Ag as a main component, a Pt—Au alloy, an Au—Pd alloy, a Pt—Ag alloy and a Pt—Ni alloy,
wherein the third electrode has a lower oxidation-catalytic activity toward the combustible gas component than the second electrode.

9. The gas sensor according to claim 8, wherein said third electrode has a two-layer structure comprising:
a porous main electrode layer comprising a Pt—Au alloy or Pt; and
a porous surface electrode layer covering the main electrode, said surface electrode layer comprising an Au-containing metal containing Au as a main component.

10. The gas sensor according to claim 8, wherein the area of the first electrode is smaller than that of the third electrode.

11. The gas sensor according to claim 8, comprising a pumping cell unit including said first oxygen pumping element and a sensor cell unit including said oxygen concentration detection element, said pumping cell unit being arranged separately from said sensor cell unit, said second processing space and said combustible gas component concentration detection element; and said pumping cell unit and said sensor cell unit being joined and integrated with each other via a bonding material.

12. The gas sensor according to claim 11, wherein said pumping cell unit comprises a pump-cell-side fitting portion and said sensor cell unit comprises a sensor-cell-side fitting portion engaged with the pump-cell-side fitting portion; and said pumping cell unit and said sensor cell unit are joined and integrated with each other via engagement of the pump-cell-side fitting portion with the sensor-cell-side fitting portion.

13. The gas sensor according to claim 1, wherein said oxygen concentration detection element comprises an oxygen concentration cell element comprising an oxygen-ion conductive solid electrolyte having electrodes formed on opposing surfaces thereof, one of the electrodes of the oxygen concentration cell element is exposed to said first processing space and is defined as a first electrode;

the electrode of said combustible gas component concentration detection element exposed to said second processing space is defined as a second electrode; and said gas sensor further comprising a wall portion and a porous metal layer other than said second electrode formed on said wall portion, said second processing space being defined in part by said porous metal layer, and said porous metal layer being exposed to said second processing space and serving as said oxidation catalyst.

14. The gas sensor according to claim 1, wherein said oxygen concentration detection element comprises an oxygen concentration cell element comprising an oxygen-ion conductive solid electrolyte having electrodes formed on opposing surfaces thereof, one of the electrodes of the oxygen concentration cell element is exposed to said first processing and is defined as a first electrode; and the first electrode comprises a porous metal of Pt—Au alloy, Pt—Ag alloy or Pt.

15. A gas sensor system comprising:

a gas sensor comprising:

a first processing space and a first gas passage for introducing a measurement gas containing oxygen and a combustible gas component into said first processing space;

a second processing space and a second gas passage for introducing a gas contained in said first processing space into said second processing space;

an oxygen concentration detection element for measuring the oxygen concentration of the gas contained in said first processing space;

an oxygen pumping element comprising an oxygen-ion conductive solid electrolyte having electrodes formed on opposing surfaces thereof, said oxygen pumping element pumping out oxygen from said first processing space or pumping oxygen into said first processing space;

an oxidation catalyst for accelerating combustion of a combustible gas component contained in the gas which has been introduced into said second processing space from said first processing space via the second gas passage; and a combustible gas component concentration detection element for providing information regarding the concentration of the combustible gas component of the measurement gas comprising an oxygen-ion conductive solid electrolyte having electrodes formed on opposing surfaces thereof, one said electrodes being exposed to said second processing space, said combustible gas component concentration detection element having an output current which varies according to the amount of oxygen consumed by combustion of the combustible gas component when a constant voltage is applied to the electrodes of the combustible gas component concentration detection element, to thereby provide information regarding the concentration of the combustible gas component of the measurement gas;

oxygen pumping operation control means controlling said oxygen pumping element by passing a pumping current therethrough such that the oxygen concentration of the measurement gas introduced into said first processing space and measured by said oxygen concentration detection elements falls within a range of $10^{-12}$ atm to $10^{-6}$ atm; and a voltage source for applying a constant voltage to the electrodes of said combustible gas component concentration detection element.

16. The gas sensor system according to claim 15, comprising a voltage source for applying a voltage to the electrodes of said combustible gas component concentration detection element in a polarity such that the electrode exposed to said second processing space becomes negative.

17. The gas sensor system according to claim 15, further comprising correction means for correcting the output of said combustible gas component concentration detection element based on the oxygen concentration of the measurement gas as determined by the pumping current of said oxygen pumping element.

18. The gas sensor system according to claim 15, wherein said oxygen concentration detection element comprises an oxygen concentration cell element comprising an oxygen-ion conductive solid electrolyte having electrodes formed on opposing surfaces thereof, one of the electrodes defined as a first electrode serves as a detection electrode and is exposed to said first processing space, the other electrode serves as a self-generating oxygen reference electrode for passing a small pumping current between said detection electrode and said oxygen reference electrode in a direction such that oxygen is pumped toward the side of said oxygen reference electrode, to thereby establish a reference oxygen concentration of a predetermined level within the oxygen reference electrode by the oxygen pumped into the oxygen reference electrode;

the oxygen reference electrode also serves as an electrode of said combustible gas component concentration detection element, and the other electrode of the combustible gas component concentration detection element is exposed to said second processing space and is defined as a second electrode; and the gas sensor system further comprising a current limit circuit for limiting within a predetermined range the current flowing between the second electrode and the oxygen reference electrode of said combustible gas component concentration detection element.

* * * * *